US006392013B1

(12) United States Patent
Seed et al.

(10) Patent No.: US 6,392,013 B1
(45) Date of Patent: *May 21, 2002

(54) REDIRECTION OF CELLULAR IMMUNITY BY PROTEIN TYROSINE KINASE CHIMERAS

(75) Inventors: Brian Seed, Boston; Charles Romeo, Belmont; Waldemar Kolanus, Watertown, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/889,712

(22) Filed: Jul. 7, 1997

Related U.S. Application Data

(60) Division of application No. 08/394,912, filed on Feb. 24, 1995, now Pat. No. 6,004,811, which is a continuation of application No. 08/093,210, filed on Jul. 16, 1993, now abandoned, which is a continuation-in-part of application No. 07/847,566, filed on Mar. 6, 1992, which is a continuation-in-part of application No. 07/665,961, filed on Mar. 7, 1991, now abandoned.

(51) Int. Cl.[7] ............................. C12P 21/02; C12P 21/04
(52) U.S. Cl. ..................... 530/350; 536/23.5; 435/69.7; 435/252.3; 435/320.1; 424/192.1
(58) Field of Search ..................... 530/350; 536/23.5; 435/252.3, 320.1, 69.7; 424/192.1

(56) References Cited

U.S. PATENT DOCUMENTS

| 4,690,915 A | 9/1987 | Rosenberg |
| 4,946,778 A | 8/1990 | Ladner et al. |
| 5,091,513 A | 2/1992 | Huston et al. |
| 5,225,538 A | 7/1993 | Capon et al. |
| 5,336,603 A | 8/1994 | Capon et al. |
| 5,359,046 A | 10/1994 | Capon et al. |
| 5,439,819 A | 8/1995 | Littman et al. |
| 5,504,000 A | 4/1996 | Littman et al. |
| 5,686,281 A | 11/1997 | Roberts |
| 5,712,149 A | 1/1998 | Roberts |

FOREIGN PATENT DOCUMENTS

| EP | 0 180 878 | 5/1986 |
| EP | 0 314 317 | 5/1989 |
| EP | 0 325 262 | 7/1989 |
| EP | 0 340 793 | 11/1989 |
| EP | 0 394 827 | 10/1990 |
| JP | 10-63394 | 3/1989 |
| NZ | 224379 | 12/1990 |
| WO | WO 86/01533 | 3/1986 |
| WO | WO 88/01649 | 3/1988 |
| WO | WO 90/04640 | 5/1990 |
| WO | WO 90/11360 | 10/1990 |
| WO | WO 91/10736 | 7/1991 |
| WO | WO 92/10591 | 6/1992 |
| WO | WO 92/15322 | 9/1992 |
| WO | WO 93/19163 | 9/1993 |
| WO | WO 95/02686 | 1/1995 |
| WO | WO 95/21528 | 8/1995 |
| WO | WO 96/26265 | 8/1996 |

OTHER PUBLICATIONS

Roussel et al., Antibody–Induced Mitogenicity Mediated by a Chimeric CD2–c–fms Receptor. Molecular and Cellular Biology. vol. 10, No. 5, pp. 2407–2412. See entire documant, May 1999.*
Shapira–Nahor et al., "Isotype Specificity of Antigen–Specific Helper Clone In Vivo," *J. Immunol.* 139:35–41 (1987).
Stancovski et al., "Targeting of T Lymphocytes to Neu/HER2–Expressing Cells Using Chimeric Single Chain Fv Receptors" *The Journal of Immunology* 151:6577–6582 (1993).
Harding et al., "CD28–B7 Interactions Allow the Induction of CD8+ Cytotoxic T Lymphocytes in the Absence of Exogenous Help" *J. Exp. Med.* 177:1791–1796 (1993).
Abraham and Veillette, Mol. Cell. Biol. 10:5197–5206, 1990.
Accolla, J. Exp. Med., 157:1053–1058, 1983.
Al–Jaufy et al., Infection and Immunity, 62:956–960, 1994.
Alberola–lla et al., J. Immunology 151(9):4423–4430, (Nov. 1, 1993).
Anderson et al., "CD3–negative Natural Killer Cells Express TCR as Part of a Novel Molecular Complex," Nature 341:159–162, 1989.
Anderson et al., "Fc Receptor Type III (CD16) is Included in the NK Receptor Complex Expressed by Human Natural Killer Cells," Proc. Natl. Acad. Sci. USA 87: 2274–2278, 1990.
Appleby et al., Cell 70:751–763, 1992.
Aruffo and Seed, EMBO J. 6:3313, 1987.
Aruffo et al., "Molecular Cloning of a CD28 cDNA by a High–Efficiency COS Cell Expression System," Proc. Natl. Acad. Sci. USA 84: 8573–8577, 1987.
Ashorn et al., J. Virol. 64:2149 1990.
Aullo et al., EMBO J. 11:575–583, 1992.
Bachmann et al. "In vivo versus in vitro assays for assessment of T–and B–cell function" Current Opinion in Immunology, vol. 8 (2), 320–328, 1994.

(List continued on next page.)

Primary Examiner—Lorraine Spector
Assistant Examiner—Eileen B. O'Hara
(74) Attorney, Agent, or Firm—Clark & Elbing LLP

(57) ABSTRACT

Disclosed is a method of directing a cellular response in a mammal by expressing in a cell of the mammal a chimeric receptor which causes the cells to specifically recognize and destroy an infective agent, a cell infected with an infective agent, a tumor or cancerous cell, or an autoimmune-generated cell. The chimeric receptor includes an extracellular portion which is capable of specifically recognizing and binding the target cell or target infective agent, and (b) an intracellular portion of a protein-tyrosine kinase which is capable of signalling the therapeutic cell to destroy a receptor-bound target cell or a receptor-bound target infective agent. Also disclosed are cells which express the chimeric receptors and DNA encoding the chimeric receptors.

6 Claims, 11 Drawing Sheets

OTHER PUBLICATIONS

Balk and Terhorst, Immunol. Ser. 45:411–416, 1989.
Baniyash et al., J. Biol. Chem. 263:9874–9878, 1988.
Bauer et al., Proc. Natl. Acad. Sci. USA 88:3842–3846, 1991.
Becker et al., "Expression of a Hybrid Immunoglobulin–T Cell Receptor Protein in Transgenic Mice," Cell 58 911–921, 1989.
Becker et al., "Messenger RNA in Cells Infected with Vaccinia Virus," Biochemistry 51: 577–585, 1964.
Bell et al., Mol. Cell. Biol. 12:5548–5554, 1992.
Berke et al., "T Lymphocyte–Mediated Cytolysis—A Comprehensive Theory," Mechanisms of Cell Mediated Cytotoxicity, 57–68, 1982.
Berke, "Lymphocyte–Triggered Internal Target Disintegration," Immunology Today 12:396–399, 1991.
Berke, "Cytotoxic T–Lymphocytes; How Do They Function?," Immunological Rev. 72:5–42, 1983.
Berkhout et al., "Transfection of Genes Encoding the T Cell Receptor–Associated CD3 complex into COS Cells Results in Assembly of the Macromolecular Structure." Journal of Biological Chemsitry 263: 8528–8536, 1988.
Blank et al., "Complete Structure and Expression in Transfected Cells of High Affinity IgE Receptor," Nature 337:187–189, 1989.
Blumberg et al., "Antibody–Dependent Cell–Mediated Cytotoxicity Against Cells Infected with the Human Immunodeficiency Virus." Journal of Infectious Diseases 156:878–883, 1987.
Blumberg et al., J. Biol. Chem. 265:14036, 1990.
Bolen et al., Adv. Cancer Res. 57:103–149, 1991.
Boyle et al., "A Dominant Selectable Marker for the Construction of Recombinant Poxviruses," Gene 65:123–128, 1988.
Breitmeyer et al., J. Immunol. 138:726, 1987.
Brown, Washngton Post, A1 and A22 (Dec. 8, 1995).
Buonocore et al., "Prevention of HIV–1 glycoprotein Transport by Soluble CD4 Retained in the Endoplasmic Reticulum," Nature 345:625–628, 1990.
Burkhardt et al., Proc. Natl. Acad. Sci. USA 88:7410–7414, 1991.
Byrn et al., "Biological Properties of a CD4 Immunoadhesin," Nature 344:667–670, 1990.
Campbell and Sefton, Mol. Cell. Biol. 12:2315–2321, 1992.
Campbell and Sefton, EMBO J. 9:2125–2131, 1990.
Capon et al., "Designing CD4 Immunoadhesins for AIDS Therapy," Nature 337:525–531, 1989.
Carr et al., "Protein and Carbohydrate Structural Analysis of a Recombinant Soluble CD4 Receptor by Mass Spectrometry," Journal of Biological Chemistry 264: 21286–21295, 1989.
Carter et al., Proc. Natl. Acad. Sci. USA 88:2745–2749, 1991.
Chakrabarti et al., "Expression of the HTLV–III Envelope Gene by a Recombinant Vaccinia Virus," Nature 320: 535–537, 1986.
Chan et al., Proc. Natl. Acad. Sci. USA 88:9166–9170, 1991.
Chan et al., Cell 71:649–662, 1992.
Chao et al., J. Biol. Chem. 264:5812–5817, 1989.
Chaudhary et al., "Selective Killing of HIV–Infected Cells by Recombinant Human CD4–Pseudomonas Exotoxin Hybrid Protein," Nature 335:369–372, 1988.
Clark et al., "T Lymphocyte–Mediated Cytolysis–A Comprehensive Theory," II. Lytic vs. NonLytic Interactions of T Lymphocytes, Mechanisms of Cell Mediated Cytotoxicity, 69–73.
Clark et al., Science 258:123–126, 1992.
Clark and Ledbetter, Adv. Cancer Res. 52:81–149, 1989.
Clayton et al., Proc. Natl. Acad. Sci. USA 88:5202–5206, 1991.
Clayton et al., "Characterization of Thymus–Derived Lymphocytes Expressing Antigen Receptor Isoforms: Analysis by Gene Transfection," J. Exp. Med. 172:1243–1253, 1990.
Cline, "Gene Therapy: Current Status and Future Directions," Schweiz, Med. Wschr. 116:1459–1464, 1986.
Coghlan et al., New Scientist 14–15 (Nov. 25, 1995).
Cooke and Perlmutter, New Biol. 1:66–74, 1989.
Cooke et al., Cell 65:281–291, 1991.
Dalgleish et al., "The CD4(T4) Antigen is an Essential Component of the Receptor for the AIDS Retrovirus," Nature 312:763–767, 1984.
Davidson et al., J. Exp. Med. 175:1483–1492, 1992.
Deen et al., "A Soluble Form of CD4(T4) Protein Inhibits AIDS Virus Infection," Nature 331: 82–84, 1988.
DeFranco, Eur. J. Biochem. 210:381–388, 1992.
Denny et al., "A Chromosome 14 Inversion in a T–Cell Lymphoma is Caused by Site–Specific Recombination Between Immunoglobulin and T–Cell Receptor Loci," Nature 320:549–551, 1986.
Doyle et al., "Interaction Between CD4 and Class II MHC Molecules Mediates Cell Adhesion," Nature 330: 256–259, 1987.
Earl et al., "Removal of Cryptic Poxvirus Transcription Termination Signals from the Human Immunodeficiency Virus Type 1 Envelope Gene Enhances . . . ," Journal of Virology, 64:2448–2451, 1990.
Eiseman and Bolen, Nature 355:78–80, 1992.
Falkner et al., "*Escherichia coli* gpt Gene Provides Dominant Selection for Vaccinia Virus Open Reading Frame Expression Vectors," Journal of Virology, 62:1849–1854, 1988.
Fanger et al., "Cytotoxicity Mediated by Human Fc Receptors for IgG," Immunology Today 10: 92–99, 1989.
Fisher et al., "HIV Infection is Blocked in Vitro by Recombinant Soluble CD4," Nature 331:76–78, 1988.
Fleit et al., Proc. Natl. Acad. Sci. USA 79:3275–3279, 1982.
Frank et al., "Structural Mutations of the T Cell Receptor Chain and Its Role in T Cell Activation," Science 249: 174–177, 1990.
Friedman et al., "Expression of a Truncated Viral Trans–activator Selectively Impedes Lytic Infection by its Cognate Virus," Nature 335:452–454, 1988.
Gassmann et al., Eur. J. Immunol. 22:283–286, 1992.
Gay et al., "Functional Interaction Between Human T–Cell Protein CD4 and the Major Histocompatibility Complex HLA–DR Antigen," Nature 328: 626–629, 1987.
Glaichenhaus et al., Cell 64:511–520, 1991.
Gold et al., Nature 345:810–813, 1990.
Goldsmith and Weiss, Proc. Natl. Acad. Sci. USA 84:6879–6883, 1987.
Golstein et al., Immunol. Rev. 68:5–42, 1982.
Gorny et al., Proc. Natl. Acad. Sci. USA 86:1624, 1989.
Goverman et al., "Chimeric Immunoglobulin–T Cell Receptor Proteins Form Functional Receptors: Implications for T–Cell Receptor Complex Formation and Activation," Cell 60:929–939, 1990.

Grant et al., Science 258:1903–1910, 1992.
Green et al., "Mutational Analysis of HIV–1 Tat Minimal Domain Peptides: Identification of Trans–Dominant Mutants That Suppress HIV–LTR–Driven Gene Expression," Cell 58: 215–223, 1989.
Gross et al., "Expression of Immunoglobulin–T–Cell Receptor Chimeric Molecules as Functional Receptors with Antibody–Type Specificity," Proc. Natl. Acad. Sci. USA 86:10024–10028, 1989.
Grynkiewicz et al., "A New Generation of $Ca^2$ Indicators with Greatly Improved Fluorescence Properties," Journal of Biological Chemistry 260:3440–3450, 1985.
Hatakeyama et al., Science 252:1523–1528, 1991.
Haynes et al., "Scientific and Social Issues of Human Immunodeficiency Virus Vaccine Development," Science 260:1279–1293, 1993.
He et al., Blood 79(9):2296–2302 (May 1, 1992).
Hermanson et al., "B29: A Member of the Immunoglobulin Gene Superfamily Exclusively Expressed on B–Lineage Cells," Proc. Natl. Acad. Sci. USA, 85:6890–6894, 1988.
Hibbs et al., "Mechanisms for Regulating Expression of Membrane Isoforms of FcRIII (CD16) ," Science 246: 1608–1611, 1989.
Hildreth et al., "Involvement of a Leukocyte Adhesion Receptor (LFA–1) in HIV–Induced Syncytium Formation," Science 244:1075–1078, 1989.
Hoffenbach et al., J. Immunol. 142(2):452–462, 1989.
Huang et al., J. Biol. Chem. 267:5467–5473, 1992.
Hussey et al., "A Soluble CD4 Protein Selectively Inhibits HIV Replication and Syncytium Formation," Nature 331:78–81, 1988.
Hutchcroft et al., J. Biol. Chem. 266:14846–14849, 1991.
Hutchcroft et al., Proc. Natl. Acad. Sci. USA 89:9107–9111, 1992.
Hutchcroft et al., J. Biol. Chem. 267:8613–8619, 1992.
Irving et al., J. Exp. Med. 177:1093–1103, 1993.
Irving and Weiss, Cell 64:891–901, 1991.
Jenkins et al., "T–Cell Unresponsiveness in Vivo and In Vitro: Fine Specificity of Induction and Molecular Characterization of the Unresponsive State," Immunological Reviews 95:113–135, 1987.
Jin et al., "Molecular Cloning of the CD3 Subunit Identifies a CD3 Related Product in Thymus–Derived Cells," Proc. Natl. Acad. Sci. USA 87: 3319–3323, 1990.
Johnston et al., Science 260:1286–1293, 1993.
Jones et al., Nature 323: 346–349 (Sep. 25, 1986).
June et al., Proc. Natl. Acad. Sci. USA 87:7722–7726, 1990.
June et al., J. Immunol. 144:1591–1599, 1990.
Karnitz et al., Mol. Cell. Biol. 12:4521–4530, 1992.
Kinet, Cell 57:351–354, 1989.
Klatzmann et al., "T–Lymphocyte T4 Molecule Behaves as the Receptor for Human Retrovirus LAV," 312:767–768, 1984.
Koga et al., Eur. J. Immunol. 16:1643–1646, 1986.
Kohler et al., Eur. J. Immunol. 6:292–295, 1976.
Kohler et al., Eur. J. Immunol. 6:511, 1976.
Kohler et al., Nature 256:495–497, 1975.
Kolanus et al., "T–Cell Activation by Clustered Tyrosine Kinases, " Cell 74:1–20, 1993.
Kolanus et al., EMBO J. 11:4861–4868, 1992.
Krissansen et al., "Primary Structure of the T3 Subunit of the T3/T Cell Antigen Receptor Complex Deduced from cDNA sequences: Evolution of the T3 Subunits," EMBO J. 5:1799–1808, 1986.
Kroczek et al., Nature 322:181–184, 1986.
Kurosaki et al., "A Single Amino Acid in the Glycosyl Phosphatidylinositol Attachment Domain Determines the Membrane Topology of FcR III," Nature 342:805–807, 1989.
Kuster et al., "Characterization and Expression of the Gene for the Human Fc Receptor Subunit," Journal of Biological Chemistry, 6448–6452.
Kuwana et al., "Expression of Chimeric Receptor Composed of Immunoglobulin–Derived V Regions and T–Cell Receptor–Derived C Regions," Biochemical and Biophysical Research Comm. 149: 960–968, 1987.
Lamarre et al., "The MHC–Binding and gpI 120–Binding Functions of CD4 are Separable," Science 245:743–746, 1989.
Lane et al., J. Immunol. 146:715–722, 1991.
Lanier et al., "Co–Association of CD3 with a Receptor (CD16) for IgG Fc on Human Natural Killer Cells," Nature 342:803–805, 1989.
Lawson et al., "Separate Genes Encode Functionally Equivalent ADP/ATP Carrier Proteins in *Saccharomyces cerevisiae*," Journal of Biological Chemistry 263:14812–14818, 1988.
Letourneur and Klausner, Proc. Natl. Acad. Sci. USA 88:8905–8909, 1991.
Letourner and Klausner, Science 255:79–82, 1992.
Li et al., Mol. Cell. Biol. 12:3176–3182, 1992.
Lifson et al., "Induction of CD4–Dependent Cell Fusion by the HTLV–III/LAV Envelope Glycoprotein," Nature 323:725–728, 1986.
Lifson et al., "Synthetic CD4 Peptide Derivatives That Inhibit HIV Infection and Cytopathicity," Science 241: 712–716, 1988.
Lin et al., FASEB J. 7:1070–1080, 1993.
Littman et al.,Cell 40:237–247, 1985.
Luo and Sefton, Mol. Cell. Biol. 12:4724–4732, 1992.
Maddon et al., "The T4 Gene Encodes the AIDS Virus Receptor and is Expressed in the Immune System and the Brain," Cell 47:333–348, 1986.
Maggio et al., Proc. Natl. Acad. Sci. 90:3103–3107, 1993.
Malim et al., "Functional Dissection of the HIV–1 Rev Trans–Activator–Derivation of a Trans–Dominant Repressor of Rev Function," Cell 58: 205–214, 1989.
Marasco et al., J. Clin. Invest. 90:1467, 1992.
Marshall, Science 269:1050–1055, 1995.
McDougal et al., "Binding of HTLV–III/LAV to T4 T–Cells by a Complex of the 110K Viral Protein and the T4 Molecule," Science 231: 382–385, 1986.
Mellman, Curr. Opin. Immunol. 1:16–25, 1988.
Mercep et al., "T–Cell CD3 Heterodimer Expression and Coupling to Phosphoinositide Hydrolysis," Science 242: 571–574, 1988.
Mercep et al., "Activation–Driven Programmed Cell Death and T–Cell Receptor Expression," Science 246:1162–1165, 1989.
Miettinen et al., Cell 58:317–327, 1989.
Moebius et al., J. Exp. Med. 176:507–517 1992.
Morley et al., "The Lysine Residue in the Membrane–Spanning Domain of the Chain is Necessary for Cell Surface Expression of the T Cell Antigen Receptor," J. Exp. Med. 166:1971–1978, 1988.
Muller et al., Mol. Cell. Biol. 12:5087–5093, 1992.
Mustelin et al., Science 247:1584–1587, 1990.
Nakumara et al., Exp. Hematology 21:236–242, 1993.

Nishebe et al., Science 250:1253–1256, 1990.
Oettgen et al., "A T3–like Protein Complex Associated with the Antigen Receptor on Murine T Cells," Nature 320:272–275, 1986.
Ohashi et al., "Reconstitution of an Active Surface T3/T–cell Antigen Receptor by DNA Transfer," Nature 316: 606–609, 1985.
Orloff et al., J. Biol. Chem. 264:14812–14817, 1989.
Orloff et al., "Family of Disulphide–Linked Dimers Containing the ζ and η Chains of the T–Cell Receptor and the Gamma Chain of Fc Receptors, " Nature 347:189–191, 1990.
Ostergaard et al., "The Role of $Ca^2$ in Activation of Mature Cytotoxic T Lymphocytes for Lysis," Journal of Immunology 139:3573–3579, 1987.
Park et al., Proc. Natl. Acad. Sci. USA 88:5453–5456, 1991.
Park et al., J. Biol. Chem. 266:24237–24240, 1991.
Pendergast et al., Cell 66:161–171, 1991.
Perussia et al., "Murine Natural Killer Cells Express Functional Fc Receptor II Encoded by the FcRa Gene," J. Exp. Med. 170:73–86, 1989.
Potocmjak et al., Science 215:1637, 1982.
Qui et al., "Organization of the Human and Mouse Low–Affinity FcR Genes: Duplication and Recombination," Science 248:732–735, 1990.
Ra et al., "Complete Structure of the Mouse Mast Cell Receptor for IgE (FcRI) and Surface Expression of Chimeric Receptors (Rat–Mouse–Human) on Transfected Cells," Journal of Immunology 264:15323–15327, 1989.
Ra et al., "A Macrophage Fc Receptor and the Mast Cell Receptor for IgE Share an Identical Subunit," Nature 341:752–754, 1989.
Rabinovitch et al., "Heterogeneity Among T Cells in Intracellular Free Calcium Responses After Mitogen Stimulation with PHA or Anti–CD3 . . . ," Journal of Immunology 137:952–961, 1986.
Ravetch and Kinet, Annu. Rev. Immunol. 9:457–492, 1991.
Ravetch et al., "Alternative Membrane Forms fo FcRIII (CD16) on Human Natural Kiler Cells and Neutrophils," J. Exp. Med. 170:481–497, 1989.
Reidel et al, EMBO J. 8:2934–2954, 1989.
Reidel et al., Nature 324:68–70, 1986.
Reinherz and Schlossman, Cell 19:821–827, 1980.
Reinherz et al., "Separation of Functional Subsets of Human T–Cells by a Monoclonal Antibody," Proc. Natl. Acad. Sci. USA 76: 4061–4065, 1979.
Reth, Nature 338:383–384, 1989.
Rice et al., "Vaccinia Virus Induces Cellular mRNA Degradation," Journal of Virology 47:529–539, 1983.
Romeo et al., Cell 64:1037–1046, 1991.
Romeo et al., "Sequence Requirements for Induction of Cytolysis by the T Cell Antigen/Fc Receptor Chain," Cell 68: 889–897, 1992.
Romeo et al., Cold Spring Harbor Symp. Quant. Biol. 57:117–125, 1992.
Rosenberg et al., "Gene Transfer into Humans–Immunotherapy of Patients with Advanced Melanoma, Using Tumor–Infiltrating Lymphocytes Modified by Retroviral Gene Transduction," New Eng. J. of Med. 323:570–578, 1990.
Rosenberg, "Adoptive Immunotherapy for Cancer," Scientific American, 61–69, May 1990.
Rudd et al., Proc. Natl. Acad. Sci. USA 85:5190–5194, 1988.
Sakuguchi et al., "B Lymphocyte Lineage–Restricted Expression of mb–1, a Gene with CD3–like Structural Properties," EMBO J. 7:3457–3464, 1988.
Samelson et al., Cell 43:223–231, 1985.
Samelson et al., Proc. Natl. Acad. Sci. USA 87:4358–4362, 1990.
Sancho et al., J. Biol. Chem. 264:20760, 1989.
Sattentau et al., "The CD4 Antigen: Physiological Ligand and HIV Receptor," Cell 52: 631–633, 1988.
Schwartz, "Costimulation of T Lymphocytes: The Role of CD28, CTLA–4, and B7/BB1 in Interleukin–2 Production and Immunotherapy," Cell 71:1065–1068, 1992.
Schwartz, "A Cell Culture Model for T Lymphocyte Clonal Anergy," Science 243:1349–1356, 1990.
Secrist et al., J. Biol. Chem. 266:12135–12139, 1991.
Secrist et al., J. Biol. Chem. 268:5886–5893, 1993.
Sekigawa et al., J. Virol. 64:5194–5198, 1990.
Shaw et al., Cell 59:627–636, 1989.
Shen et al., Mol. Immunol. 26:959–969, 1989.
Sleckman et al., "Expression and Function of CD4 in a Murine T–cell Hybridoma," Nature 328:351–353, 1987.
Smith et al., "Blocking of HIV–1 Infectivity by a Soluble, Secreted Form of the CD4 Antigen," Science 238:1704–1707, 1987.
Sodroski et al., "A Second Post–Transcriptional Trans–Activator Gene Required for HTLV–III Replication," Nature 321:412–417, 1986.
Sodroski et al., "Role of the HTLV–III/LAV Envelope in Syncytium Formation and Cytopathicity," Nature 322: 470–477, 1986.
Stanley et al., J. Immunol. 145:2189–2198, 1990.
Stefanova et al., Science 254:1016–1019, 1991.
Stein et al., Cell 70:741–750, 1992.
Straus and Weiss, Cell 70:585–593, 1992.
Suda et al., Blood 79(9):2288–2295 (May 1, 1992).
Sugie et al., Proc. Natl. Acad. Sci. USA 88:9132–9135, 1991.
Sussman et al., "Failure to Synthesize the T Cell CD3 Chain: Structure and Function of a Partial T Cell Receptor Complex," Cell 52:85–95, 1988.
Taniguchi et al., J. Biol. Chem. 266:15790–15796, 1991.
Thomas and Samelson, J. Biol. Chem. 267:1231–12322, 1992.
Till et al., "HIV–Infected Cells Are Killed by cCD4–Ricin A Chain," Science 242:1166–1168, 1988.
Timson Gauen et al., Mol. Cell. Biol. 12:5438–5446, 1992.
Tirosh et al., "T–Lymphocyte–Mediated Cytolysis as an Excitatory Process of the Target," Cellular Immunology 95:113–123, 1985.
Traunecker et al., "Highly Efficient Neutralization of HIV with Recombinant CD4–Immunoglobulin Molecules," Nature 339:68–70, 1989.
Traunecker et al., "Soluble CD4 Molecules Neutralize Human Immunodeficiency Virus Type 1," Nature 331:84–86, 1988.
Trenn et al., "Exocytosis of Cytolytic Granules May Not Be Required for Target Cell Lysis by Cytotoxic T–Lymphocytes," Nature 330:72–74, 1987.
Trono et al., "HIV–1 Gag Mutants Can Dominantly Interfere with the Replication of the Wild–Type Virus," Cell 59: 113–120, 1989.
Tsygankov et al., J. Biol. Chem. 267:18259–18262, 1992.

Tunnacliffe et al., "Physical Linkage of Three CD3 Genes on Human Chromosome 11," The EMBO J. 6:2953–2967, 1987.
Turner et al., Cell 60:755–765, 1990.
Unkeless et al., Annu. Rev. Immunol. 6:251–281, 1988.
Valentin et al., "The Leukocyte Adhesion Glycoprotein CD18 Participates in HIV–1–Induced Syncytia Formation in Monocytoid and T Cells," Journal of Immunology 144:934–937, 1990.
Van Den Elsen et al., "Exon/Intron Organization of the Genes Coding for the Chains of the Human and Murine T–cell Receptor/T3 Complex," Proc. Natl. Acad. Sci. USA 83: 2944–2948, 1986.
Veillette et al., Cell 55:301–308, 1988.
Wacholtz et al., "Anti–CD3–Stimulated $Ca^{2+}$ Signal in Individual Human Peripheral T Cells," Journal of Immunology 150:5338–5349, 1993.
Wands et al., Gastroenterology 80:225–232, 1981.
Wange et al., J. Biol. Chem. 267:11685–11688, 1992.
Watanabe et al., "Effect of Recombinant Soluble CD4 in Rhesus Monkeys Infected with Simian Immunodeficiency Virus of Macaques," Nature 337:267–270, 1989.
Webb et al., Science 249:1295–1297, 1990.
Wegener et al., "The T Cell Receptor/CD3 Complex is Composed of at Least Two Autonomous Transduction Modules," Cell 68:83–95, 1992.
Weiss et al., Annu. Rev. Genet. 25:487–510, 1991.
Weiss et al., Cold Spring Harbor Symp. Quant. Biol. 57:107–116, 1992.
Weiss et al., "Requirement for the Coexpression of T3 and the T Cell Antigen Receptor on a Malignant Human T Cell Line," J. Exp. Med. 160:1284–1299, 1984.
Weiss et al., "Variable and Conserved Neutralization Antigens of Human Immunodeficiency Virus," Nature 234: 574–575, 1986.
Weiss et al., J. Immunol. 133:123–128, 1984.
Weissman et al., "A New Subunit of the Human T–Cell Antigen Receptor Complex," Nature 324:480–482, 1986.
Weissman et al., "Role of the Zeta Chain in the Expression of the T Cell Antigen Receptor: Genetic Reconstitution Studies," EMBO J. 8:3651–3656, 1989.
Weissman et al., "Molecular Cloning of the Zeta Chain of the T Cell Antigen Receptor," Science 239:1018–1021, 1988.
Weissman et al., "Molecular Cloning and Chromosomal Localization of the Human Receptor Chain: Distinction from the Molecular CD3 Complex ," Proc. Natl. Acad. Sci. USA 85:9709–9713, 1988.
Wong et al., Oncogene 7:2407–2415, 1992.
Yague et al., "The T Cell Receptor: The $\alpha$ and $\beta$ Chains Define Idiotype, and Antigen and MHC Specifity Cell," 42:81–87, 1985.
Yamanashi et al., Science 251:192–194, 1991.
Yeh et al., J. Immunol. 138:91–97, 1987.
Yoffe et al., "Fusion as a Mediator of Cytolysis in Mixtures of Uninfected CD4+ Lymphocytes and Cells Infected by Human Immunodeficiency Virus," Proc. Natl. Acad. Sci. USA 84:1429–1433, 1987.
Yokoyama and Shevach, Year Immunol. 4:110–146, 1989.
Young et al., A Calcium– and Perforin– Independent Pathway of Killing Mediated by Murine Cytolytic Lymphocytes, J. Exp. Med. 166:1894–1899, 1987.
Zettimeissl et al., "Expression and Characterization of Human CD4: Immunoglobulin in Fusion Proteins," DNA and Cell Biology 9:347–353, 1990.
Zioncheck et al., J. Biol. Chem. 261:15637–15643, 1986.
Zioncheck et al., J. Biol. Chem. 263:19195–19202, 1988.
Bernard et al., "High–affinity interleukin 2 binding by an oncogenic hybrid interleukin 2–epidermal growth factor receptor molecule," Proc. Natl. Acad. Sci. USA 84:2125–2129 (1987).
Yarden et al., "Growth Factor Receptor Tyrosine Kinases," Ann. Rev. Biochem. 57:443–478 (1988).
Alexander et al., "Kinases and phosphatases in T–cell activation," Immunology Today 10:200–205 (1989).
Ashwell et al., "Genetic and Mutational Analysis of the T–Cell Antigen Receptor," Ann. Rev. Immunol. 8:139–167 (1990).
Verhoeyen et al., "Reshaping Human Antibodies: Grafting an Antilysozyme Activity," Science 259:1534–1536 (1988).

* cited by examiner

```
human    1  MADSANHLPFFFGNITREEAEDYLVQGGMSDGLYLLRQSRNYLGGFALSV   50
            |||||||||||||.||||||||||||||||||||||||||||||||||||
porcine  1  MADSANHLPFFFGQITREEAEDYLVQGGMSDGLYLLRQSRNYLGGFALSV   50

51  AHGRKAHHYTIERELNGTYAIAGGRTHASPADLCHYHSQESDGLVCLLKK  100
            |:||||||||||||||||||||.|||||.|||:|||||||| ||||||||.
        51  AYDRKAHHYTIERELNGTYAISGGRTHGSPAELCHYHSQELDGLVCLLKN  100

101  PFNRPQGVQPKTGPFEDLKENLIREYVKQTWNLQGQALEQAIISQKPQLE  150
            ||.||| |||||||||||||||||||||||||||||||||||||||||||
       101  PFNRPPGVQPKTGPFEDLKENLIREYVKQTWNLQGQALEQAIISQKPQLE  150

151  KLIATTAHEKMPWFHGKISREESEQIVLIGSKTNGKFLIRARDNNGSYAL  200
            ||||||||||||||||||||:|||||||||||||||||||||| ||||||
       151  KLIATTAHEKMPWFHGKISRDESEQIVLIGSKTNGKFLIRARD.NGSYAL  199

201  CLLHEGKVLHYRIDKDTGKLSIPEGKKFDTLWQLVEHYSYKADGLLRVL   250
            |||||||||||||||||||||||| ||.|||||||||||.||||||||
       200  GLLHEGKVLHYRIDKDTGKLSIPGGKNFDTLWQLVEHYSYKSDGLLRVL   249

251  TVPCQKIGTQ.GNVNFGGRPQLPGSHPATWSAGGIISRIKSYSFPKPGHR  299
            |||||||| | ||.|  |||||..|||||||||||||||||||||||||
       250  TVPCQKIGGQTGNDSF..RPQLPSAHPATWSAGGIISRIKSYSFPKPGHR  297

300  KSSPAQGNRQESTVSFNPYEPELAPWAADKGPQREALPMDTEVYESPYAD  349
            |.|..|||| || ||:||||.: .||  :: .||||||||||||||||||
       298  KASSPQGNRPESLVSYNPYESDRGPWANEREAQREALPMDTEVYESPYAD  347

350  PEEIRPKEVYLDRKLLTLEDKELGSNFGTVKKGYYQMKKVVKTVAVKIL   399
            |||||||||||||||||||||||||||||||||||||||||||||||||
       348  PEEIRPKEVYLDRKLLTLEDKELGSNFGTVKKGYYQMKKVVKTVAVKIL   397

400  KNEANDPALKDELLAEANVMQQLDNPYIVRMIGICEAESWMLVMEMAELG  449
            ||||||||||||||||||||||||||||||||||||||||||||||||||
       398  KNEANDPALKDELLAEANVMQQLDNPYIVRMIGICEAESWMLVMEMAELG  447

450  PLNKYLQQNRHVKDKNIIELVHQVSMGMKYLEESNFVHRDLAARNVLLVT  499
            |||||||||||||||||||||||||||||||||| |||||||||||||||
       448  PLNKYLQQNRHVKDKNIIELVHQVSMGMKYLEECNFVHRDLAARNVLLVT  497

500  QHYAKISDFGLSKALRADENYYKAQTHGKWPVKWYAPECINYYKFSSKSD  549
            ||||||||||||||||||||||||||||||||||||||||||||||||||
       498  QHYAKISDFGLSKALRADENYYKAQTHGKWPVKWYAPECINYYKFSSKSD  547

550  VWSFGVLMWEAFSYGQKPYRGMKGSEVTAMLEKGERMGCPAGCPREMYDL  599
            |||||||||||||||||||||||||||.||||||||||||.|||·||||:|
       548  VWSFGVLMWEAFSYGQKPYRGMKGSEVSAMLEKGERMGCPPGCPREMYEL  597

600  MNLCWTYDVENRPGFAAVELRLRNYYYDVVN  630
            |.|||||||||||| |||||||||||||||||
       598  MTLCWTYDVENRPGFVAVELRLRNYYYDVVN  628
```

FIG. 7A

CD16/7/syk

REDIRECTION OF CELLULAR IMMUNITY BY PROTEIN TYROSINE KINASE CHIMERAS

This application is a divisional of Seed et al., U.S. Ser. No. 08/394,912, filed Feb. 24, 1995, now U.S. Pat. No. 6,004,811, which is a continuation of Seed et al., U.S. Ser. No. 08/093,210, filed Jul. 16, 1993, now abandoned, which is a continuation-in-part of application Ser. No. 07/847,566, filed Mar. 6, 1992, which is a continuation-in-part of application Ser. No. 07/665,961, filed Mar. 7, 1991, now abandoned.

This invention was made with Government support under NIH grant AI27849. The government has certain rights in the invention.

FIELD OF THE INVENTION

The invention concerns functional protein-tyrosine kinase chimeras which are capable of redirecting immune system function. More particularly, it concerns the regulation of lymphocytes, macrophages, natural killer cells or granulocytes by the expression in said cells of chimeras which cause the cells to respond to targets recognized by the chimeras. The invention also concerns functional protein-tyrosine kinase chimeras which are capable of directing therapeutic cells to specifically recognize and destroy either cells infected with a specific infective agent, the infective agent itself, a tumor cell, or an autoimmune-generated cell. More particularly, the invention relates to the production of protein-tyrosine kinase chimeras capable of directing cytotoxic T lymphocytes to specifically recognize and lyse cells expressing HIV envelope proteins. The invention therefore provides a therapy for diseases such as AIDS (Acquired Immunodeficiency Syndrome) which are caused by the HIV virus.

BACKGROUND OF THE INVENTION

T cell recognition of antigen through the T cell receptor is the basis of a range of immunological phenomena. The T cells direct what is called cell-mediated immunity. This involves the destruction by cells of the immune system of foreign tissues or infected cells. A variety of T cells exist, including "helper" and "suppressor" cells, which modulate the immune response, and cytotoxic (or "killer") cells, which can kill abnormal cells directly.

A T cell that recognizes and binds a unique antigen displayed on the surface of another cell becomes activated; it can then multiply, and if it is a cytotoxic cell, it can kill the bound cell.

Autoimmune disease is characterized by production of either antibodies that react with host tissue or immune effector T cells that are autoreactive. In some instances, autoantibodies may arise by a normal T- and B-cell response activated by foreign substances or organisms that contain antigens that cross react with similar compounds in body tissues. Examples of clinically relevant autoantibodies are antibodies against acetylcholine receptors in myasthenia gravis; and anti-DNA, anti-erythrocyte, and anti-platelet antibodies in systemic lupus erythematosus.

HIV and Immunopathogenesis

In 1984 HIV was shown to be the etiologic agent of AIDS. Since that time the definition of AIDS has been revised a number of times with regard to what criteria should be included in the diagnosis. However, despite the fluctuation in diagnostic parameters, the simple common denominator of AIDS is the infection with HIV and subsequent development of persistent constitutional symptoms and AIDS defining diseases such as a secondary infections, neoplasms, and neurologic disease. *Harrison's Principles of Internal Medicine,* 12th ed., McGraw Hill (1991).

HIV is a human retrovirus of the lentivirus group. The four recognized human retroviruses belong to two distinct groups: the human T lymphotropic (or leukemia) retroviruses, HTLV-1 and HTLV-2, and the human immunodeficiency viruses, HIV-1 and HIV-2. The former are transforming viruses whereas the latter are cytopathic viruses.

HIV-1 has been identified as the most common cause of AIDS throughout the world. Sequence homology between HIV-2 and HIV-1 is about 40% with HIV-2 being more closely related to some members of a group of simian immunodeficiency viruses (SIV). See Curran, J. et al., *Science,* 329:1357–1359 (1985); Weiss, R. et al., *Nature,* 324:572–575 (1986).

HIV has the usual retroviral genes (env, gag, and pol) as well as six extra genes involved in the replication and other biologic activities of the virus. As stated previously, the common denominator of AIDS is a profound immunosuppression, predominantly of cell-mediated immunity. This immune suppression leads to a variety of opportunistic diseases, particularly certain infections and neoplasms.

The main cause of the immune defect in AIDS, has been identified as a quantitative and qualitative deficiency in the subset of thymus-derived (T) lymphocytes, the T4 population. This subset of cells is defined phenotypically by the presence of the CD4 surface molecule, which has been demonstrated to be the cellular receptor for HIV. Dalgleish et al., *Nature,* 312:763 (1984). Although the T4 cell is the major cell type infected with HIV, essentially any human cell that expresses the CD4 molecule on its surface is capable of binding to and being infected with HIV.

Traditionally, CD4+ T cells have been assigned the role of helper/inducer, indicating their function in providing an activating signal to B cells, or inducing T lymphocytes bearing the reciprocal CD8 marker to become cytotoxic/suppressor cells. Reinherz and Schlossman, *Cell,* 19:821–827 (1980); Goldstein et al., *Immunol. Rev.,* 68:5–42, (1982).

HIV binds specifically and with high affinity, via a stretch of amino acids in the viral envelope (gp120), to a portion of the V1 region of the CD4 molecule located near its N-terminus. Following binding, the virus fuses with the target cell membrane and is internalized. Once internalized it uses the enzyme reverse transcriptase to transcribe its genomic RNA to DNA, which is integrated into the cellular DNA where it exists for the life or the cell as a "provirus."

The provirus may remain latent or be activated to transcribe mRNA and genomic RNA, leading to protein synthesis, assembly, new virion formation, and budding of virus from the cell surface. Although the precise mechanism by which the virus induces cell death has not been established, it is felt that the major mechanism is massive viral budding from the cell surface, leading to disruption of the plasma membrane and resulting osmotic disequilibrium.

During the course of the infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia and death. The failure of the host anti-viral antibodies to arrest the progression of the disease represents one of the most vexing and alarming aspects of the infection, and augurs poorly for vaccination efforts based upon conventional approaches.

Two factors may play a role in the efficacy of the humoral response to immunodeficiency viruses. First, like other RNA viruses (and like retroviruses in particular), the immunodeficiency viruses show a high mutation rate in response to host immune surveillance. Second, the envelope glycoproteins themselves are heavily glycosylated molecules presenting few epitopes suitable for high affinity antibody binding. The poorly antigenic target which the viral envelope presents, allows the host little opportunity for restricting viral infection by specific antibody production.

Cells infected by the HIV virus express the gp120glycoprotein on their surface. Gp120 mediates fusion events among $CD4^+$ cells via a reaction similar to that by which the virus enters the uninfected cells, leading to the formation of short-lived multinucleated giant cells. Syncytium formation is dependent on a direct interaction of the gp120 envelope glycoprotein with the CD4 protein. Dalgleish et al., supra; Klatzman, D. et al., *Nature*, 312:763 (1984); McDougal, J. S. et al., *Science,* 231:382 (1986); Sodroski, J. et al., *Nature,* 322:470 (1986); Lifson, J. D. et al., *Nature,* 323:725 (1986); Sodroski, J. et al., *Nature,* 321:412 (1986).

Evidence that the CD4-gp120 binding is responsible for viral infection of cells bearing the CD4 antigen includes the finding that a specific complex is formed between gp120 and CD4. McDougal et al., supra. Other investigators have shown that the cell lines, which were noninfective for HIV, were converted to infectable cell lines following transfection and expression of the human CD4 cDNA gene. Maddon et al., *Cell,* 46:333–348 (1986).

Therapeutic programs based on soluble CD4 as a passive agent to interfere with viral adsorption and syncytium-mediated cellular transmission have been proposed and successfully demonstrated in vitro by a number of groups (Deen et al., *Nature,* 3321:82–84 (1988); Fisher et al., *Nature,* 331:76–78 (1988); Hussey et al., *Nature* 331:78–81 (1988); Smith et al., *Science,* 238:1704–1707 (1987); Traunecker et al., *Nature,* 331:84–86 (1988)); and CD4 immunoglobulin fusion proteins with extended halflives and modest biological activity have subsequently been developed (Capon et al., *Nature,* 337:525–531 (1989); Traunecker et al. *Nature,* 339, 68–70 (1989); Byrn et al., *Nature,* 344:667–670 (1990); Zettlmeissl et al., *DNA Cell Biol.* 9:347–353 (1990)). Although CD4 immunotoxin conjugates or fusion proteins show potent cytotoxicity for infected cells in vitro (Chaudhary et al., *Nature,* 335:369–372 (1988); Till et al., *Science,* 242:1166–1168 (1988)), the latency of the immunodeficiency syndrome makes it unlikely that any single-treatment therapy will be effective in eliminating viral burden, and the antigenicity of foreign fusion proteins is likely to limit their acceptability in treatments requiring repetitive dosing. Trials with monkeys affected with SIV have shown that soluble CD4, if administered to animals without marked CD4 cytopenia, can reduce SIV titer and improve in vitro measures of myeloid potential (Watanabe et al., *Nature,* 337:267–270 (1989)). However a prompt viral reemergence was observed after treatment was discontinued, suggesting that lifelong administration might be necessary to prevent progressive immune system debilitation.

Cell Surface Receptor-Associated Protein-Tyrosine Kinases

The initial impetus for engagement of cellular effector programs in the immune system is often cell recognition of clustered ligands. Among the receptors known to transmit activating signals upon aggregation are the B cell and T cell antigen receptors (DeFranco, 1992, Eur. J. Biochem. 210:381–388; Weiss, 1991, Annu. Rev. Genet. 25:487–510), members of the IgG and IgE Fc receptor families (Fanger et al., 1989, Immunol. Today 10:92–99; Ravetch and Kinet, 1991, Annu. Rev. Immunol. 9:457–492) and a number of accessory receptors, including CD2, CD4, CD8 and CD28 in T cells (Yokoyama and Shevach, 1989, Year Immunol. 4:110–146), CD19, CD20, CD21 and CD40 in B cells (Clark and Ledbetter, 1989, Adv. Cancer Res. 52:81–149), and CD44, CD45 and CD58 in monocytes (Webb et al., 1990, Science 249:1295–1297). In addition, a large number of phospholipid linked proteins promote cellular activation in an antigen receptor-dependent manner when crosslinked on the surface of T cells (Balk and Terhorst, 1989, Immunol. Ser. 45:411–416; Kroczek et al., 1986, Nature 322:181–184; Yeh et al., 1987, J. Immunol. 138:91–97; Yokoyama and Shevach, 1989, Year Immunol. 4:110–146).

At present it is not clear how a simple physical event, aggregation, results in a clearly distinguished physiological signal. Engagement of cellular effector programs mediated by the T cell and B cell antigen receptors, and various forms of Fc receptor, can be mimicked by crosslinking of chimeric proteins bearing the intracellular domains of individual chains of the receptor complexes (Irving and Weiss, 1991, Cell 64:891–901; Kolanus et al., 1992, EMBO J. 11:4861–4868; Letourneur and Klausner, 1991, Proc. Natl. Acad. Sci. USA 88:8905–8909; Letourneur and Klausner, 1992, Science 255:79–82; Romeo and Seed, 1991, Cell 64:1037–1046; Wegener et al., 1992, Cell 68:83–95). The minimal effective trigger element appears to require a phylogenetically conserved (Reth, 1989, Nature 338:383–384) peptide sequence containing two tyrosine residues separated by 10 or 11 residues and embedded in a hydrophilic, typically acidic context (Romeo et al., 1992, Cell 68:889–897; Irving et al., 1993, J. Exp. Med. 177, 1093–1103). Clustering of receptors bearing this element initiates an activation cascade for which protein tyrosine kinase (PTK) activity appears to be essential; PTK inhibitors block both early events in B and T cell activation such as calcium mobilization and the later sequelae of cytokine release and cellular proliferation (June et al., 1990, J. Immunol. 144:1591–1599; Lane et al., 1991, J. Immunol. 146:715–722; Mustelin et al., 1990, Science 247:1584–1587; Stanley et al., 1990, J. Immunol. 145:2189–2198). Although the more distal consequences of receptor activation differ according to cell type, the early events are strikingly similar among cells from disparate hematopoietic lineages. For example the rapid increases in PTK activity observed following crosslinking of the B cell antigen receptor (Gold et al., 1990, Nature 345:810–813; Campbell and Sefton, 1990, EMBO J. 9:2125–2131), the T cell antigen receptor (June, C. H., et al. 1990, Proc. Natl. Acad. Sci. USA 87:7722–7726; June, C. H., et al., 1990, J. Immunol. 144:1591–1599) and the high affinity IgE receptor (Eiseman and Bolen, 1992, Nature 355:78–80; Li et al., 1992, Mol. Cell. Biol. 12:3176–3182) all have among their early phosphorylation targets the γ isoform of phosphatidylinositol-specific phospholipase C (Carter et al., 1991, Proc. Natl. Acad. Sci. USA 88:2745–2749; Li et al., 1992, Mol. Cell Biol. 12:3176–3182; Park et al., 1991, J. Biol. Chem. 266:24237–24240; Park et al., 1991, Proc. Natl. Acad. Sci. USA 88:5453–5456; Secrist et al., 1991, J. Biol. Chem. 266:12135–12139; Weiss et al., 1991, Annu. Rev. Genet. 25:487–510), which is directly activated by tyrosine phosphorylation (Nishibe et al., 1990, Science 250:1253–1256).

The PTK activities known thus far to associate with cell surface receptors fall in two classes: those belonging to the family of Src proto-oncogene-related kinases and those related to the recently characterized Syk kinase. Among the former, the Fyn kinase has been shown to associate with the T cell receptor (Gassmann et al., 1992, Eur. J. Immunol. 22:283–286; Samelson et al., 1990, Proc. Natl. Acad. Sci. USA 87:4358–4362), the Lyn, Fyn, Blk and Lck kinases have been reported to associate with the B cell IgM receptor, (Burkhardt et al., 1991, Proc. Natl. Acad. Sci. USA 88:7410–7414; Campbell and Sefton, 1992, Mol. Cell. Biol. 12:2315–2321; Yamanashi et al., 1991, Science 251:192–194), and the Lyn and Yes kinases have been shown to associate with the high affinity IgE receptor (Eiseman and Bolen, 1992, Nature 355:78–80; Hutchcroft et al., 1992, Proc. Natl. Acad. Sci. USA 89:9107–9111; Hutchcroft, J. E., et al., 1992, J. Biol. Chem. 267:8613–8619). The mechanism of the observed association has not been established in detail, but preliminary data suggest that the intracellular domains of receptor complex chains may physically associate with Src family kinases (Clark et al., 1992, Science 258:123–126; Timson Gauen et al., 1992, Mol. Cell. Biol. 12:5438–5446). At present it is not clear whether these associations are direct or indirect.

To date, the most compelling evidence for the importance of Src family kinases in cell activation has been developed from the study of the Fyn and Lck kinases in T cells. Overexpression of Fyn in transgenic mice leads to an antigen hyperresponsive phenotype in the resulting T cells, while overexpression of a catalytically inactive form blocks T cell receptor mediated proliferation (Cooke et al., 1991, Cell 65:281–291). Thymic T cells isolated from mutant mice lacking Fyn kinase activity show a profound defect in the ability to mount a proliferative response in response to treatment with a combination of phorbol ester plus either anti-CD3 antibody or Concanavalin A (Appleby et al., 1992, Cell 70:751–763; Stein et al., 1992, Cell 70:741–750). Splenic T cells isolated from such mice show a less severe, but substantial, attenuation of the cell activation response (Appleby et al., 1992, Cell 70:751–763; Stein et al., 1992, Cell 70:741–750).

In T cells the Lck kinase associates indirectly with the TCR through the CD4 and CD8 coreceptors (Rudd et al., 1988, Proc. Natl. Acad. Sci. USA 85:5190–5194; Shaw et al., 1989, Cell 59:627–636; Turner et al., 1990, Cell 60:755–765; Veillette et al., 1988, Cell 55:301–308). Overexpression of Lck in an antigen-responsive cell line potentiates receptor sensitivity in similar fashion to that seen with Fyn (Abraham and Veillette, 1990, Mol. Cell. Biol. 10:5197–5206; Davidson et al., 1992, J. Exp. Med. 175:1483–1492; Luo and Sefton, 1992, Mol. Cell. Biol. 12:4724–4732). In a CD4-dependent murine T cell hybridoma model, reconstitution of antigen-specific helper function could be achieved only with CD4 molecules which were capable of interacting with Lck (Glaichenhaus et al., 1991, Cell 64:511–520).

However the strongest evidence for the direct participation of the Lck kinase in antigen receptor-mediated signalling comes from studies of mutant cell lines which lack Lck. Two such lines have been studied, one derived from the Jurkat human T cell leukemia line (Goldsmith and Weiss, 1987, Proc. Natl. Acad. Sci. USA 84:6879–6883; Straus and Weiss, 1992, Cell 70:585–593) and the other from the murine cytotoxic T cell clone CTLL-2 (Karnitz et al., 1992, Mol. Cell. Biol. 12:4521–4530). Both Lck-negative mutant lines are defective in TCR mediated signalling, and complementation of either mutant line by transfection with an Lck expression plasmid restores responsiveness to TCR crosslinking stimuli (Karnitz et al., 1992, Mol. Cell. Biol. 12:4521–4530; Straus and Weiss, 1992, Cell 70:585–593).

Recently members of a new family of tyrosine kinases, initially represented by the closely related or identical kinases Syk (Taniguchi et al., 1991, J. Biol. Chem. 266:15790–15796) and PTK 72 (Zioncheck et al., 1986, J. Biol. Chem. 261:15637–15643; Zioncheck et al., 1988, J. Biol. Chem. 263:19195–19202), have been to shown to associate with cell surface receptors. Although PTK 72 and Syk have not been definitively proven to be identical, they share a common tissue distribution (thymus and spleen), molecular mass, and lability to proteolysis. PTK 72 has been shown to associate with the B cell IgM receptor (Hutchcroft et al., 1992. Proc. Natl. Acad. Sci. USA 89:9107–9111; Hutchcroft, J. E., et al., 1992, J. Biol. Chem. 267:8613–8619) and to be phosphorylated upon crosslinking of the receptor with anti-IgM (Hutchcroft et al., 1991, J. Biol. Chem. 266:14846–14849). A concomitant activation of the enzyme, as measured by both autophosphorylation and phosphorylation of an exogenous protein fragment, was demonstrated following surface IgM crosslinking (Hutchcroft et al., 1992, Proc. Natl. Acad. Sci. USA 89:9107–9111; Hutchcroft, J. E., et al., 1992, J. Biol. Chem. 267:8613–8619). PTK 72 is also found associated with the high affinity IgE receptor in a rat basophilic leukemia cell line (Hutchcroft et al., 1992, Proc. Natl. Acad. Sci. USA 89:9107–9111; Hutchcroft, J. E., et al., 1992, J. Biol. Chem. 267:8613–8619).

A second member of the Syk family, ZAP-70, has been shown to be a PTK associating with the zeta chain of the T cell receptor following receptor crosslinking (Chan et al., 1991, Proc. Natl. Acad. Sci. USA 88:9166–9170). Although expression in COS cells of ZAP-70, Fyn or Lck leads to modest increases in total cell tyrosine phosphate, coexpression of ZAP-70 and either Lck or Fyn leads to a dramatic increase in net tyrosine phosphorylation (Chan et al., 1992, Cell 71:649–662). If a CD8-zeta chain chimera is also present, the chimera becomes phosphorylated and ZAP-70 is found associated with it (Chan et al., 1992, Cell 71:649–662). At present it is not clear whether ZAP-70 activates the Src family kinases and/or vice versa, nor why coexpression of kinases in COS cells should lead to an apparent constitutive activation. Nonetheless the active association of ZAP-70 with crosslinked TCR suggests a role for this PTK in the propagation of the receptor response.

Unlike the Src family kinases, Syk and ZAP-70 bear two SH2 domains and no N-terminal myristoylation site (Taniguchi et al., 1991, J. Biol. Chem. 266:15790–15796; Chan et al., 1992, Cell 71:649–662). A natural expectation for the mechanism of kinase-receptor association is that the two SH2 domains bind the two tyrosines of the antigen receptor trigger motifs once they are phosphorylated. However, at present this is remains merely a hypothesis.

SUMMARY OF THE INVENTION

The present invention demonstrates the feasibility of creating chimeras between the intracellular domain of a protein-tyrosine kinase molecule and an extracellular domain which is capable of fulfilling the task of target recognition. In particular, clustering of chimeras bearing Syk or ZAP-70 kinase sequences triggers calcium mobilization. Aggregation of Syk chimera alone, or coaggregation of chimeras bearing Fyn or Lck and ZAP-70 kinases, suffices to initiate cytolytic effector function. Such effector function facilitates the specific recognition and destruction of undesirable target cells, for example, pathogens, pathegen-infected cells, tumor cells, or autoimmune cells.

Any number of useful chimeric molecules according to the invention may be constructed. For example, the formation of chimeras consisting of the intracellular portion of a protein-tyrosine kinase joined to the extracellular portion of a suitably engineered antibody molecule allows the target recognition potential of an immune system cell to be specifically redirected to the antigen recognized by the extracellular antibody portion. Thus with an antibody portion capable of recognizing some determinant on the surface of a pathogen, immune system cells armed with the chimera would respond to the presence of the pathogen with the effector program appropriate to their lineage, e.g., helper T lymphocytes would respond by cytotoxic activity against the target, and B lymphocytes would be activated to synthesize antibody. Macrophages and granulocytes would carry out their effector programs, including cytokine release, phagocytosis, and reactive oxygen generation. Similarly, with an antibody portion capable of recognizing tumor cells, the immune system response to the tumor would be beneficially elevated. With an antibody capable of recognizing immune cells having an inappropriate reactivity with self determinants, the autoreactive cells could be selectively targeted for destruction.

Although these examples draw on the use of antibody chimeras as a convenient expository tool, the invention is not limited in scope to antibody chimeras, and indeed, the use of specific nonantibody extracellular domains may have important advantages. For example with an extracellular portion that is the receptor for a virus, bacterium, or parasite, cells armed with the chimeras would specifically target cells expressing the viral, bacterial or parasitic determinants. The advantage of this approach over the use of antibodies is that the native receptor for pathogen may have uniquely high selectivity or affinity for the pathogen, allowing a greater degree of precision in the resulting immune response. Similarly, to delete immune system cells which inappropriately react with a self antigen, it may suffice to join the antigen (either as an intact protein, in the case of B cell depletion therapies, or as MHC complex, in the case of T cell depletion therapies) to intracellular protein-tyrosine kinase chains, and thereby affect the specific targeting of the cells inappropriately responding to self determinants.

Another use of the chimeras is the control of cell populations in vivo subsequent to other forms of genetic engineering. For example, the use of tumor infiltrating lymphocytes or natural killer cells to carry cytotoxic principles to the site of tumors has been proposed. The present invention provides a convenient means to regulate the numbers and activity of such lymphocytes and cells without removing them from the body of the patient for amplification in vitro. Thus, because the intracellular domains of the chimeric receptors mediate the proliferative responses of the cells, the coordination of the extracellular domains by a variety of aggregating stimuli specific for the extracellular domains (e.g., an antibody specific for the extracellular domain) will result in proliferation of the cells bearing the chimeras.

Although the specific embodiments of the present invention comprise chimeras between the Syk or Syk and Src families of protein-tyrosine kinases, any tyrosine kinase having a similar function to these molecules could be used for the purposes disclosed here. The distinguishing features of desirable immune cell trigger molecules comprise the ability to be expressed autonomously, the ability to be fused to an extracellular domain (directly or indirectly through a transmembrane domain) such that the resultant chimera is present on the surface of a therapeutic cell, and the ability to initiate cellular effector programs upon aggregation secondary to encounter with a target ligand.

At present the most convenient method for delivery of the chimeras to immune system cells is through some form of genetic therapy. However reconstituting immune system cells with chimeric receptors by mixture of the cells with suitably solubilized purified chimeric protein would also result in the formation of an engineered cell population capable of responding to the targets recognized by the extracellular domain of the chimeras. Similar approaches have been used, for example, to introduce the intact HIV receptor, CD4, into erythrocytes for therapeutic purposes. In this case the engineered cell population would not be capable of self renewal.

The present invention relates to functional simplified protein-tyrosine kinase chimeras which are capable of redirecting immune system function. More particularly, it relates to the regulation of lymphocytes, macrophages, natural killer cells or granulocytes by the expression in said cells of chimeras which cause the cells to respond to targets recognized by the chimeras. The invention also relates to a method of directing cellular response to an infective agent, a tumor or cancerous cell, or an autoimmune generated cell. The method for directing the cellular response in a mammal comprises administering an effective amount of therapeutic cells to said mammal, said cells being capable of recognizing and destroying said infective agent, tumor, cancer cell, or autoimmune generated cell.

In another embodiment, the method of directing cellular response to an infective agent comprises administering therapeutic: cells capable of recognizing and destroying said agent, wherein the agent is a specific virus, bacteria, protozoa, or fungi. Even more specifically, the method is directed against agents such as HIV and *Pneumocystis carinii*.

To treat an HIV infection, an effective amount of chimeric-receptor expression cytotoxic T lymphocytes are administered to a patient; the lymphocytes are capable of specifically recognizing and lysing cells infected with HIV as well as circulating virus.

Thus, in one embodiment, there is provided according to the invention a method for directing cellular response to HIV infected cells, comprising administering to a patient an effective amount of cytotoxic T lymphocytes which are capable of specifically recognizing and lysing cells infected with HIV.

In yet another embodiment is provided the chimeric receptor proteins which direct the cytotoxic T lymphocytes to recognize and lyse the HIV infected cell. Yet another embodiment of the invention comprises host cells transformed with a vector comprising the chimeric receptors.

These and other non-limiting embodiments of the present invention will be apparent to those of skill from the following detailed description of the invention.

In the following detailed description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson, J. D. et al., *Molecular Biology of the Gene*, Volumes I and II, the Benjamin/Cummings Publishing Company, Inc., publisher, Menlo Park, Calif. (1987); Darnell, J. E. et al., *Molecular Cell Biology*, Scientific American Books, Inc., Publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); Maniatis, T., et al., *Molecular Cloning: A Laboratory Manual*, 2nd Ed. Cold Spring Harbor Laboratory, publisher, Cold Spring Harbor, N.Y. (1989); and *Current Protocols in Molecular Biology*, Ausubel et al., Wiley Press, New York, N.Y. (1989).

Definitions

By "cloning" is meant the use of in vitro recombination techniques to insert a particular gene or other DNA sequence into a vector molecule. In order to successfully clone a desired gene, it is necessary to employ methods for generating DNA fragments for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which comprise DNA copies of mRNA being expressed by the cell at the time the cDNA library was made. Such a cDNA library may be prepared by methods known to those of skill, and described, for example, in Maniatis et al., *Molecular Cloning: A Laboratory Manual*, supra. Generally, RNA is first isolated from the cells of an organism from whose genome it is desired to clone a particular gene. Preferred for the purpose of the present invention are mammalian, and particularly human, lymphocytic cell lines. A presently preferred vector for this purpose is the vaccinia virus WR strain.

By "vector" is meant a DNA molecule, derived, e.g., from a plasmid, bacteriophage, or mammalian or insect virus, into which fragments of DNA may be inserted or cloned. A vector will contain one or more unique restriction sites and may be capable of autonomous replication in a defined host or vehicle organism such that the cloned sequence is reproducible. Thus, by "DNA expression vector" is meant any autonomous element capable of directing the synthesis of a recombinant peptide. Such DNA expression vectors include bacterial plasmids and phages and mammalian and insect plasmids and viruses.

By "substantially pure" is meant a compound, e.g., a protein, a polypeptide, or an antibody, that is substantially free of the components that naturally accompany it. Generally, a compound is substantially pure when at least 60%, more preferably at least 75%, and most preferably at least 90% of the total material in a sample is the compound of interest. Purity can be measured by any appropriate method, e.g., column chromatography, polyacrylamide gel electrophoresis, or HPLC analysis. In the context of a nucleic acid, "substantially pure" means a nucleic acid sequence, segment, or fragment that is not immediately contiguous with (i.e., covalently linked to) both of the coding sequences with which it is immediately contiguous (i.e., one at the 5' end and one at the 3' end) in the naturally occurring genome of the organism from which the DNA of the invention is derived.

By "functional derivative" is meant the "fragments," "variants," "analogues," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof. A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional or fewer amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th et., Mack Publishing Co., Easton, Pa. (1980).

Similarly, a "functional derivative" of a receptor chimera gene of the present invention is meant to include "fragments," "variants," or "analogues" of the gene, which may be "substantially similar" in nucleotide sequence, and which encode a molecule possessing similar activity to a protein-tyrosine kinase chimera.

Thus, as used herein, a protein-tyrosine kinase chimera protein is also meant to include any functional derivative, fragments, variants, analogues, or chemical derivatives which may be substantially similar to the "wild-type" chimera and which possess similar activity (i.e., most preferably, 90%, more preferably, 70%, preferably 40%, or at least 10% of the wild-type receptor chimera's activity). The activity of a functional chimeric receptor derivative includes specific binding (with its extracellular portion) to a targeted agent or cell and resultant destruction (directed by its intracellular portion) of that agent or cell; such activity may be tested, e.g., using any of the assays described herein.

A DNA sequence encoding the chimera of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a protein-tyrosine kinase chimera-encoding sequence) are said to be operably linked if the nature of the linkage between the two DNA sequences does not (1) result in the introduction of a frame-shift mutation, (2) interfere with the ability of the promoter region sequence to direct the transcription of the receptor chimera gene sequence, or (3) interfere with the ability of the receptor chimera gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of a protein-tyrosine kinase chimera protein (or a functional derivative thereof) in either prokaryotic or eukaryotic cells, although eukaryotic (and, particularly, human lymphocyte) expression is preferred.

Antibodies according to the present invention may be prepared by any of a variety of methods. For example, cells expressing the receptor chimera protein, or a functional derivative thereof, can be administered to an animal in order to induce the production of sera containing polyclonal antibodies that are capable of binding the chimera.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–684 (1981)). In general, such procedures involve immunizing an animal with the chimera antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, J. R., et al. (*Gastroenterology* 80:225–232 (1981). The hybridoma cells obtained through such a selection are then assayed to identify clones which secrete antibodies capable of binding the chimera.

Antibodies according to the present invention also may be polyclonal, or, preferably, region specific polyclonal antibodies.

Antibodies against the chimera according to the present invention may be used to monitor the amount of chimeric receptor (or chimeric receptor-bearing cells) in a patient. Such antibodies are well suited for use in standard immunodiagnostic assay known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy.

Standard reference works setting forth general principles of immunology include Roitt, I., *Essential Immunology*, Sixth Ed., Blackwell Scientific Publications, Publisher, Oxford (1988); Kimball, J. W., *Introduction to Immunology*, Second Ed., Macmillan Publishing Co., Publisher, New York (1986); Roitt, I., et al., *Immunology*, Gower Medical Publishing Ltd., Publisher, London, (1985); Campbell, A., "Monoclonal Antibody Technology," in, Burdon, R., et al., eds., *Laboratory Techniques in Biochemistry and Molecular Biology*, Volume 13, Elsevier, Publisher, Amsterdam (1984); Klein, J., *Immunology: The Science of Self-Nonself Discrimination*, John Wiley & Sons, Publisher, New York (1982); and Kennett, R., et al., eds., *Monoclonal Antibodies, Hybridoma: A New Dimension In Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those described herein can be accomplished by the technique of anti-idiotypic screening (Potocmjak, et al., *Science* 215:1637 (1982)). Briefly, an anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

For replication, the hybrid cells may be cultivated both in vitro and in vivo. High in vivo production makes this the presently preferred method of culture. Briefly, cells from the individual hybrid strains are injected intraperitoneally into pristane-primed BALB/c mice to produce ascites fluid containing high concentrations of the desired monoclonal antibodies. Monoclonal antibodies of isotype IgM or IgG may be purified from cultured supernatants using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies include malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase.

The presence of detectably labeled antibodies also can be detected by labeling the antibodies with a radioactive isotope which then can be determined by such means as the use of a gamma counter or a scintillation counter. Isotopes which are particularly useful for the purpose of the present invention are $^3$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se.

It is also possible to detect the binding of detectably labeled antibodies by labeling the antibodies with a fluorescent compound. When a fluorescently labeled antibody is exposed to light of the proper wavelength, its presence then can be detected due to the fluorescence of the dye. Among the most commonly used fluorescent labeling compounds are fluorescein, isothiocyanate, rhodamine, phycoerythrin, phycocyanin, allophycocyanin, o-phthaldehyde and fluorescamine.

The antibodies of the invention also can be detectably labeled using fluorescent emitting metals such as $^{152}$Eu, or others of the lanthanide series. These metals can be attached to the antibody molecule using such metal chelating groups as diethyl-enteriaminepentaacetic acid (DTPA) or ethylenediaminetetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminal, isoluminol, theromatic acridinium ester, imidazole, acridinium salts, oxalate ester, and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferin, luciferase aequorin.

The antibodies and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich, immunoassays.

By the term "immunometric assay" or "sandwich immunoassay," it is meant to include simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

In the preferred mode for performing the assays it is important that certain "blockers" be present in the incubation medium (usually added with the labeled soluble antibody). The "blockers" are added to assure that nonspecific proteins, protease, or human antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e., nonspecific) antibodies of the same class or subclass (isotype) as those used in the assays (e.g., $IgG_1$, $IgG_{2a}$, IgM, etc.) can be used as "blockers." The concentration of the "blockers" (normally 1–100 μg/μl) is important, in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 μg/ml) to the buffer which contains the "blockers."

There are many solid phase immunoadsorbents which have been employed and which can be used in the present invention. Well known immunoadsorbents include glass, polystyrene, polypropylene, dextran, nylon and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

For in vivo, in vitro, or in situ diagnosis, labels such as radionuclides may be bound to antibodies according to the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}$Tc, $^{123}$I, $^{111}$IN, $^{131}$I, $^{97}$Ru, $^{67}$Cu, $^{67}$Ga and $^{68}$Ga. The antibodies of the invention can also be labeled with non-radioactive isotopes for purposes of diagnosis. Elements which are particularly useful in this manner are $^{157}$Gd, $^{55}$Mn, $^{162}$Dy, $^{52}$Cr and $^{56}$Fe.

The antigen of the invention may be isolated in substantially pure form employing antibodies according to the present invention. Thus, an embodiment of the present invention provides for substantially pure protein-tyrosine kinase chimera, said antigen characterized in that it is recognized by and binds to antibodies according to the present invention. In another embodiment, the present invention provides a method of isolating or purifying the chimeric receptor antigen, by forming a complex of said antigen with one or more antibodies directed against the receptor chimera.

The substantially pure chimera antigens of the present invention may in turn be used to detect or measure antibody to the chimera in a sample, such as serum or urine. Thus, one embodiment of the present invention comprises a method of detecting the presence or amount of antibody to protein-tyrosine kinase antigen in a sample, comprising contacting a sample containing an antibody to the chimeric antigen with detectably labeled receptor chimera, and detecting said label. It will be appreciated that immunoreactive fractions and immunoreactive analogues of the chimera also may be used. By the term "immunoreactive fraction" is intended any portion of the chimeric antigen which demonstrates an equivalent immune response to an antibody directed against the receptor chimera. By the term "immunoreactive analogue" is intended a protein which differs from the receptor chimera protein by one or more amino acids, but which demonstrates an equivalent immunoresponse to an antibody of the invention.

By "specifically recognizes and binds" is meant that the antibody recognizes and binds the chimeric receptor polypeptide but does not substantially recognize and bind other unrelated molecules in a sample, e.g., a biological sample.

By "autoimmune-generated cell" is meant cells producing antibodies that react with host tissue or immune effector T cells that are autoreactive; such cells include antibodies against acetylcholine receptors (leading, e.g., to myasthenia gravis) or anti-DNA, anti-erythrocyte, and anti-placelet autoantibodies (leading, e.g., to lupus erythematosus).

By "therapeutic cell" is meant a cell which has been transformed by a chimera of the invention so that it is capable of recognizing and destroying a specific infective agent, a cell infected by a specific agent, a tumor or cancerous cell, or an autoimmune-generated cell; preferably such therapeutic cells are cells of the hematopoietic system.

By a "target infective agent" is meant any infective agent (e.g., a virus, bacterium, protozoan, or fungus) which can be recognized by a chimeric receptor-bearing therapeutic cell. By a "target cell" is meant any host cell which can be recognized by a chimeric receptor-bearing therapeutic cell; target cells include, without limitation, host cells which are infected with a virus, bacterium, protozoan, or fungus as well as tumor or cancerous cells and autoimmune-generated cells.

By "extracellular" is meant having at least a portion of the molecule exposed at the cell surface. By "intracellular" is meant having at least a portion of the molecule exposed to the therapeutic cell's cytoplasm. By "transmembrane" is meant having at least a portion of the molecule spanning the plasma membrane. An "extracellular portion", an "intracellular portion" and a "transmembrane portion", as used herein, may include flanking amino acid sequences which extend into adjoining cellular compartments.

By "oligomerize" is meant to complex with other proteins to form dimers, trimers, tetramers, or other higher order oligomers. Such oligomers may be homo-oligomers or hetero-oligomers. An "oligomerizing portion" is that region of a molecule which directs complex (i.e., oligomer) formation.

By "cytolytic" is meant to be capable of destroying a cell (e.g., a cell infected with a pathogen, a tumor or cancerous cell, or an autoimmune-generated) cell or to be capable of destroying an infective agent (e.g., a virus).

By "immunodeficiency virus" is meant a retrovirus that, in wild-type form, is capable of infecting T4 cells of a primate host and possesses a viral morphogenesis and morphology characteristic of the lentivirus subfamily. The term includes, without limitation, all variants of HIV and SIV, including HIV-1, HIV-2, SIVmac, SIVagm, SIVmnd, SIVsmm, SIVman, SIVmand, and SIVcpz.

By "MHC-independent" is meant that the cellular cytolytic response does not require the presence of an MHC class II antigen on the surface of the targeted cell.

By a "functional cytolytic signal-transducing derivative" is meant a functional derivative (as defined above) which is capable of directing at least 10%, preferably 40%, more preferably 70%, or most preferably at least 90% of the biological activity of the wild type molecule. As used herein, a "functional cytolytic signal-transducing derivative" may act by directly signaling the therapeutic cell to destroy a receptor-bound agent or cell (e.g., in the case of an intracellular chimeric receptor portion) or may act indirectly by promoting oligomerization with cytolytic signal transducing proteins of the therapeutic cell (e.g., in the case of a transmembrane domain). Such derivatives may be tested for efficacy, e.g., using the in vitro assays described herein.

By a "functional HIV envelope-binding derivative" is meant a functional derivative (as defined above) which is capable of binding any HIV envelope protein. Functional derivatives may be identified using, e.g., the in vitro assays described herein.

Therapeutic Administration

The transformed cells of the present invention may be used for the therapy of a number of diseases. Current methods of administering such transformed cells involve adoptive immunotherapy or cell-transfer therapy. These methods allow the return of the transformed immune-system cells to the bloodstream. Rosenberg, S. A., *Scientific American*, 62 (May 1990); Rosenberg et al., *The New England Journal of Medicine*, 323 (9):570 (1990).

The pharmaceutical compositions of the invention may be administered to any animal which may experience the beneficial effects of the compounds of the invention. Foremost among such animals are humans, although the invention is not intended to be so limited.

DETAILED DESCRIPTION

The drawings will first be described.

DESCRIPTION OF THE DRAWINGS

FIG. 4A shows the percent $^{51}$Cr-chromate released from hybridoma target cells shown as a function of the ratio of effector cells (CTL expressing kinase chimera) to target cells; cells expressing receptor chimeras bearing the intracellular domains of TCR zeta chain and FcRIIB2 serve as positive and negative controls respectively. PIG. 4B shows specificity of the killing (absence of bystander killing). BW5147 cells (lacking surface anti-CD16 antibody) were loaded with $^{51}$Cr-chromate and exposed to CTL expressing kinase chimeras under the same conditions as for a parallel sample of chromate-loaded 3G8 cells (expressing anti-CD16 antibody). No detectable release of chromate was observed from the BW5147 cells.

FIG. 5A shows a cytolysis assay using CTL expressing pairs of CD16/7/kinase chimeras. FIG. 5B shows calcium response of TCR negative cells expressing pairs of CD16/7/kinase chimeras. FIG. 5C shows a cytolysis assay of CTL coexpressing a CD4/CD7/Fyn chimera and a CD16/CD7/ZAP-70 chimera. CD16/7/zeta chimera serves as the positive control, while CD16/7/FcRIIB2 chimera serves as the negative control.

FIG. 6A shows calcium response in TCR negative cells. FIG. 6B shows a redirected cytolysis assay.

FIGS. 7A, 7B, and 7C show that chimeras based on human Syk are essentially equipotent with chimeras based on porcine Syk. FIG. 7A is the sequence of human Syk and comparison with porcine Syk; the first 11 and last 7 residues are determined by the primer sequences. FIG. 7B shows calcium mobilization analysis of TCR negative cells expressing human Syk chimera. FIG. 7C shows a redirected cytolysis assay of CTL expressing human Syk chimera.

FIG. 10A shows a comparison of the activity of immunoprecipitated kinase chimeras over an incubation period of ten minutes, using immunoprecipitates isolated from crosslinked (+) or uncrosslinked (–) cells. FIG. 10B shows a time course of assimilation of phosphate label into endogenous substrates by Syk kinase chimera, with (+) or without (–) crosslinking.

T CELL ACTIVATION BY CLUSTERED TYROSINE KINASES

There now follows a description of particular embodiments of the invention. In this description, it is demonstrated that nonreceptor kinases are activated by simple clustering events. Artificial receptor kinases were created whose intracellular domains consisted of the complete Src or Syk family kinase sequences and examined for the consequences of aggregation by external crosslinking stimuli. A clear distinction emerged between the Syk and Src family kinase activities: crosslinking the latter did not lead to significant cellular activation, while crosslinking the former led to the appearance of free intracellular calcium ion and, in the case of Syk, of cytolytic potential. The failure of ZAP-70 chimeras to induce distal receptor mediated programs could be overcome by coclustering ZAP-70 chimera with either Fyn or Lck kinase chimeras. The examples now described are provided for the purpose of illustrating, not limiting, the invention.

Figure 1A:
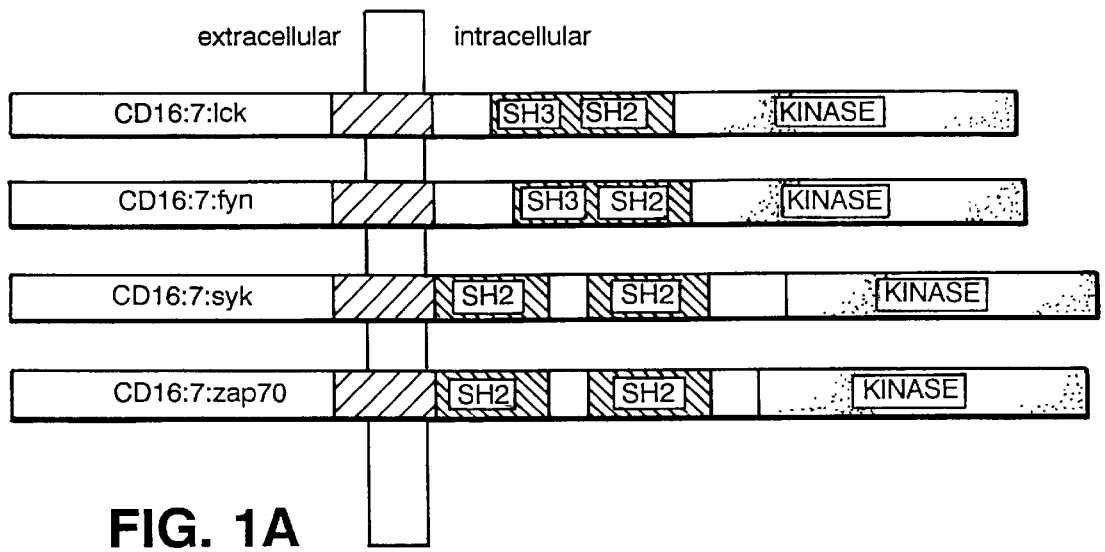
FIG. 1A is a schematic diagram showing the organization of receptor-kinase fusion proteins of the invention.
Figure 1B:
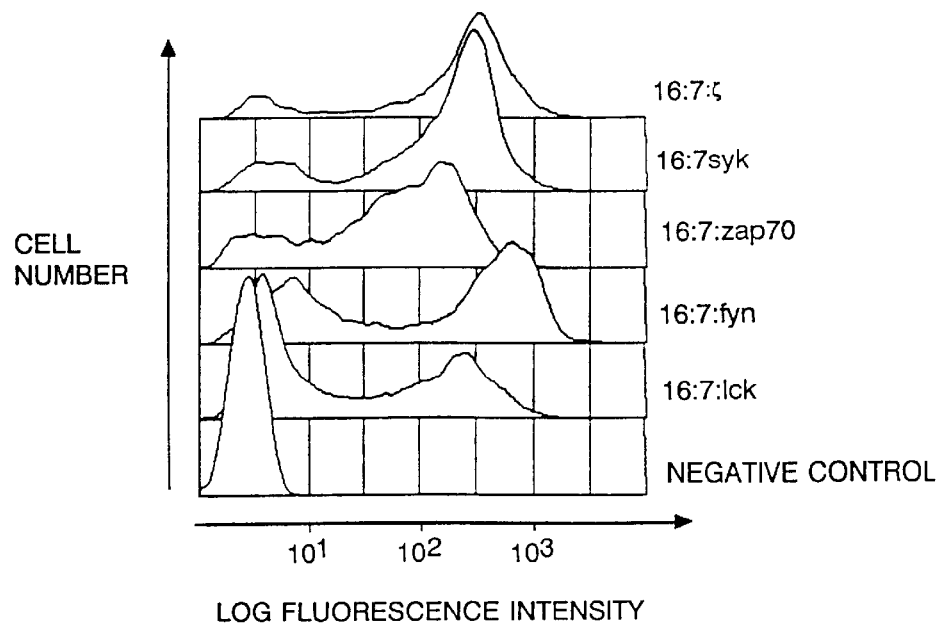
FIG. 1B shows flow cytometry results for CD16/7/zeta, CD16/7/Lck, CD16/7/Fyn(T),CD16/7/Syk and CD16/7/ZAP-70 expressed by vaccinia recombinants in Jurkat cells.
Figure 1C:
FIG. 1C shows in vitro kinase activity assay of immunoprecipitated CD16/7/zeta (negative control), CD16/7/Lck, CD16/7/Fyn (T), CD16/7/Syk and CD16/7/ZAP-70; the lower molecular mass species appearing in the Fyn chimera immunoprecipitate has yet to be identified.

Construction of Protein-tryrosine Kinase Chimeras and Demonstration of Efficacy Gene fusions encoding proteins resembling cell surface receptor kinases were constructed by appending a DNA fragment encoding the extracellular domain of the CD16 molecule to a short spacer segment encoding the juxtamembranous and transmembrane domains of CD7 joined in turn to the complete coding sequences of the human Lck (Koga et al., 1986, Eur. J. Immunol. 16:1643–1646), murine Fyn (T) (Cooke and Perlmutter, 1989, New. Biol. 1:66–74), porcine Syk (Taniguchi et al., 1991, J. Biol. Chem. 266:15790–15796) and human ZAP-70 (Chan et: al., 1992, Cell 71:649–662) tyrosine kinases (FIG. 1A). The resulting tripartite gene fusions were introduced into recombinant vaccinia viruses by homologous recombination and selection for coexpression of the *E. coli* gpt gene product. Infection of cells with the recombinants resulted in the efficient cell surface expression of all four kinase chimeras (FIG. 1B). Immunoprecipitation of the resulting protein chimeras with anti-CD16 antibodies revealed the presence of molecular species of the expected masses which were active in an in vitro phosphorylation assay (FIG. 1C).

Figure 2:
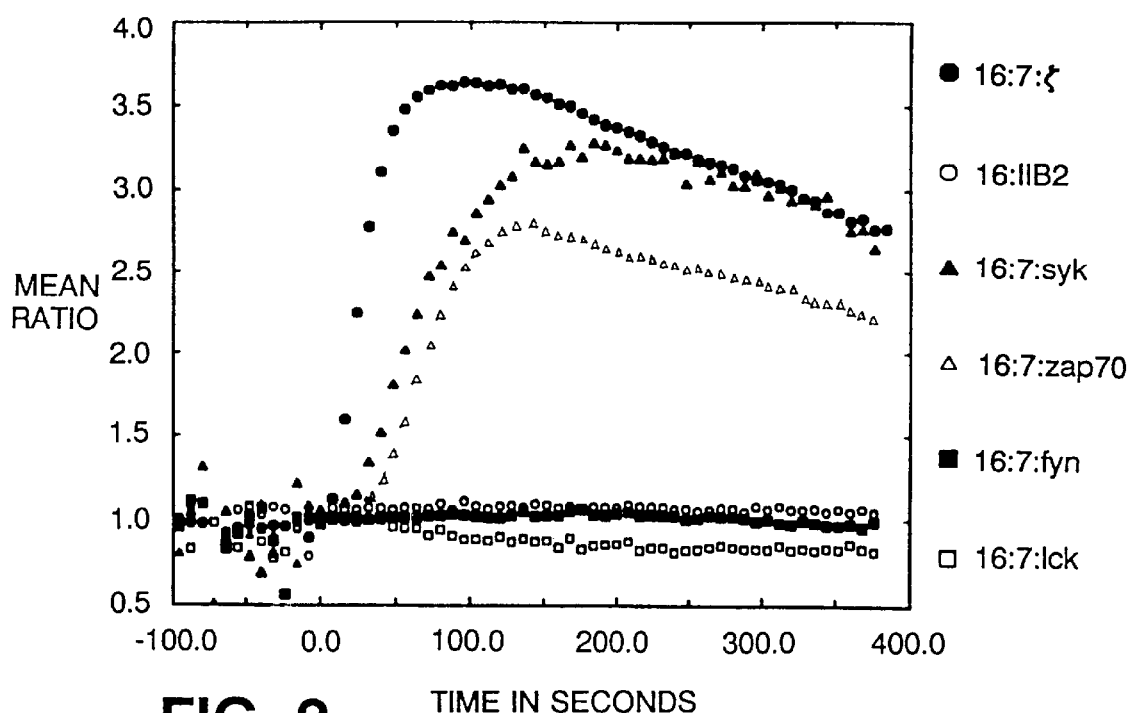
FIG. 2 shows the cytosolic calcium response triggered by crosslinking of kinase chimeras in TCR-negative Jurkat cells. The relative intracellular calcium concentration of the positive population (measured by the ratio of Indo-1 violet to blue fluorescence) is shown. Jurkat cells infected with vaccinia recombinants expressing the different fusion proteins were exposed to anti-CD16 mAb 3G8 followed by phycoerythrin conjugated goat F(ab')$_2$ antibodies to mouse IgG at time 0. Chimeras based on TCR zeta chain and FcRIIB2 serve as positive and negative controls respectively.
Figure 3:
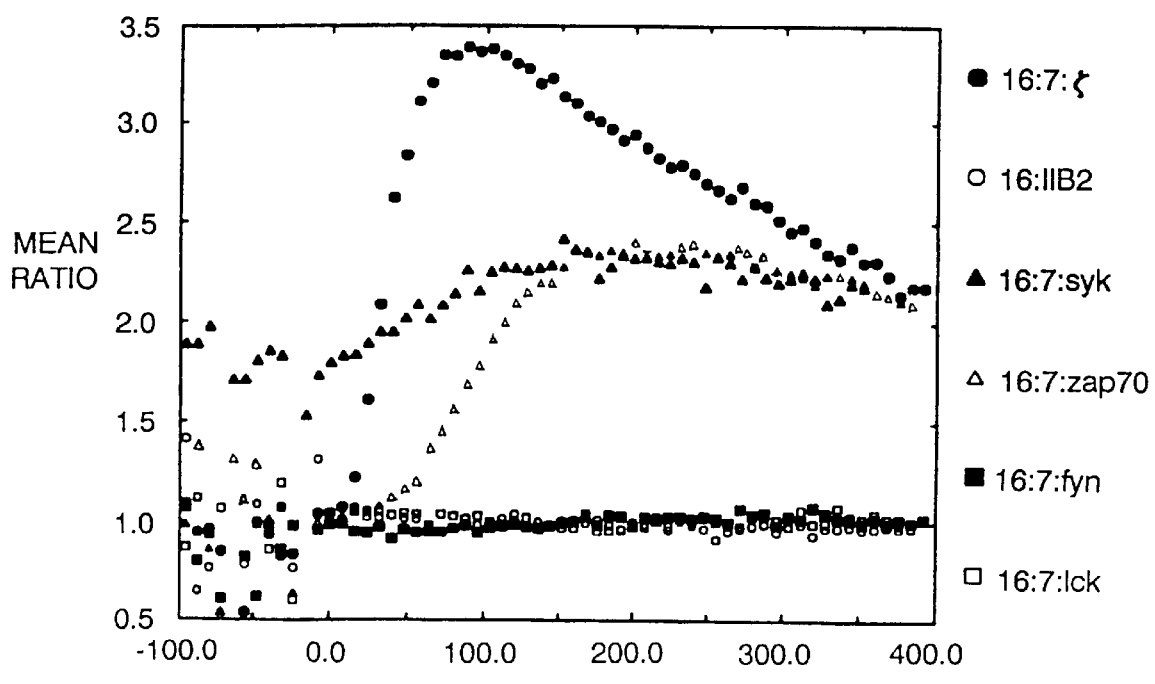
FIG. 3 shows the premature engagement of calcium response in TCR positive cells expressing Syk kinase chimera. Infection and analysis were performed as described above for FIG. 2. A substantial proportion of cells expressing Syk chimera showed a high ratio of violet to blue fluorescence prior to addition of primary antibody.

We next examined whether crosslinking of the fusion proteins would allow the accumulation of free intracellular calcium in a fashion similar to that found with fusion proteins based on T cell antigen receptor intracellular domains. To do this we infected various cells with vaccinia recombinants and measured the relative cytoplasmic calcium concentration following crosslinking of the extracellular domains with antibodies. Both spectrofluorimetric (bulk population) and flow cytometric (single cell) measurements were performed,.with cells loaded with the dye Indo-1 (Grynkiewicz et al., 1985, J. Biol. Chem. 260:3440–3450; Rabinovitch et al., 1986, J. Immunol. 137:952–961). Flow cytometric analyses were performed on data obtained from cells whose cell surface expression of CD16, as determined by phycoerythrin fluorescence intensity, fell within a relatively narrow predefined range. Although minor variations in mean fluorescence intensity were still observed within this range (due to differences in the underlying distribution of chimeras expressed by the cells), this approach allowed us to contrast the responses of cells bearing approximately the same number of receptors. FIG. 2 shows an analysis of data collected from cells of a mutational variant of the Jurkat human T cell leukemia line lacking T cell antigen receptor (Weiss and Stobo, 1984, J. Exp. Med. 160:1284–1299). In these cells neither Lck nor Fyn chimeras had the capacity to mobilize calcium following crosslinking. In several experiments clustering of the Lck fusion protein resulted in a slight decrease in resting calcium concentration, relative to the negative control, a fusion protein based on the low affinity IgG receptor FcRIIB2 intracellular domain (Kolanus et al., 1992, EMBO J. 11:4861–4868). Aggregation of fusion proteins based on both ZAP-70 and Syk was highly effective in promoting the appearance of free cytoplasmic calcium ion, roughly as effective as aggregation of a similar chimera bearing the intracellular domain of the T cell receptor zeta chain. A slight delay in onset of the calcium response was seen with both ZAP-70 and Syk kinase chimeras, relative to the time of onset of calcium mobilization by zeta chimera. In T cell receptor positive cells (FIG. 3), flux evaluation of Syk chimeras was partially confounded by a high resting concentration of free calcium ion, suggestive of a constitutive engagement of the calcium regulatory apparatus.

Figure 4A:
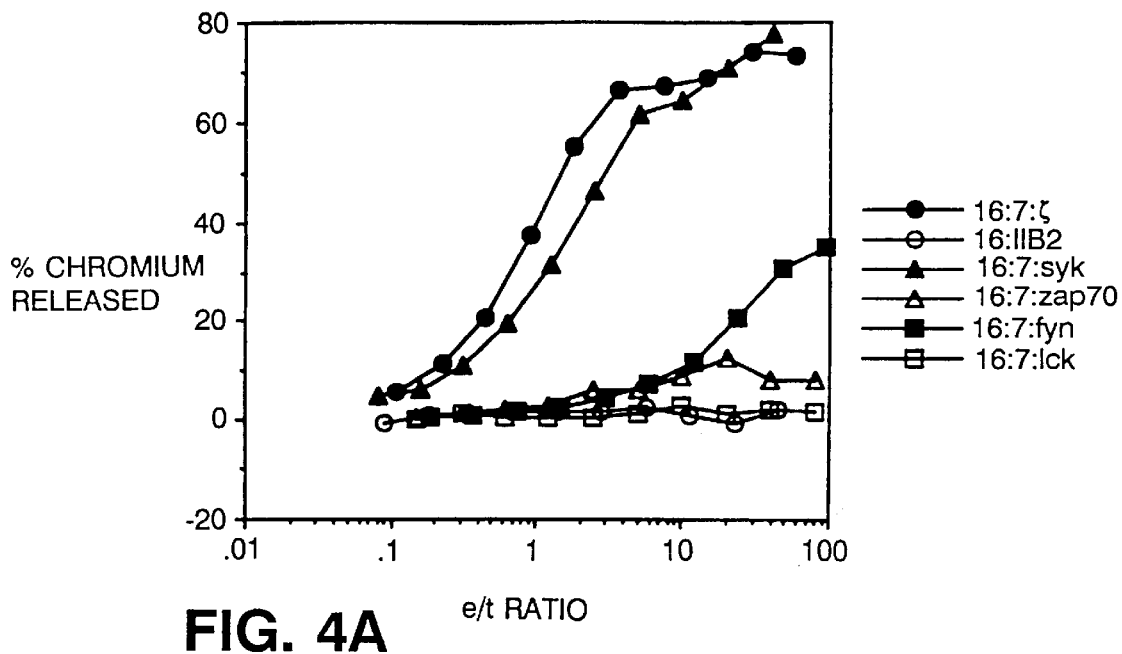
FIGS. 4A and 4B show an anti-hybridoma killing assay.
Figure 4B:
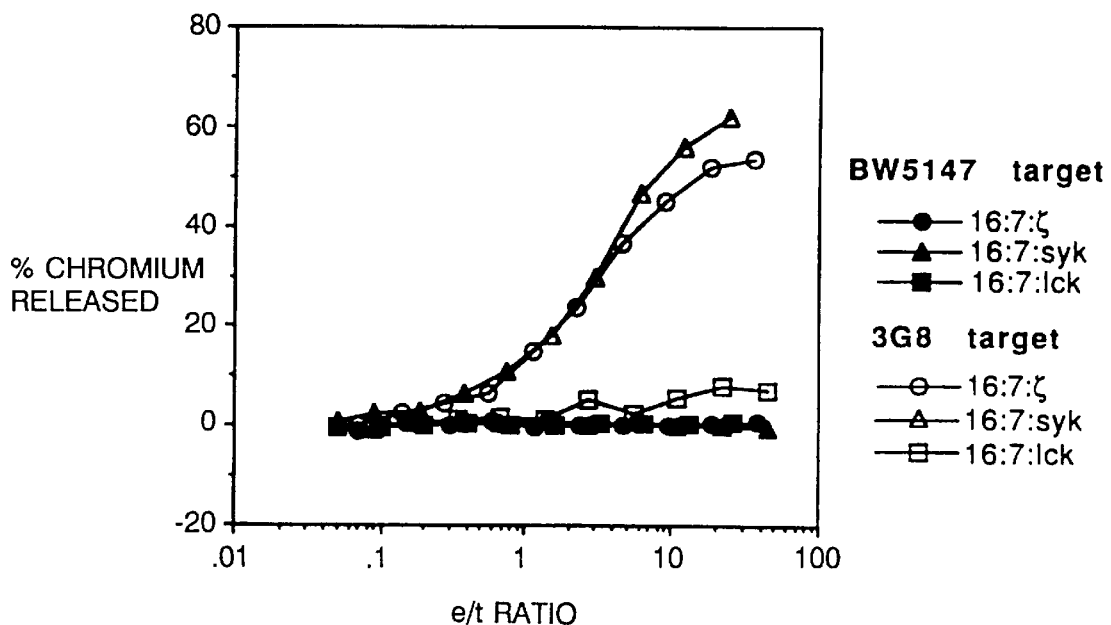

Introduction of the chimeras into a cytolytic T cell line then allowed us to assess the fusion proteins' potential to engage effector function. In this assay, anti-CD16 hybridoma cells which express cell surface IgG antibody against CD16 (Fleit et al., 1982, Proc. Natl. Acad. Sci. USA 79:3275–3279; Shen et al., 1989, Mol. Immunol. 26:959–969) are used as target cells. The hybridoma cells are labeled by incorporation of $^{51}$Cr-chromate and cosedimented with effector cells, prepared by infection of a human allospecific cytotoxic T lymphocyte (CTL) line with vaccinia recombinants expressing the CD16/CD7/kinase fusion proteins. Expression of the chimeric receptor kinases allows the infected CTL cells to bind to the target cells, and if competent, to lyse them, a process which is measured by release of the incorporated $^{51}$Cr-chromate. The relative potency of the armed CTL is determined by comparison of the ratio of effector to target cells needed to achieve a given proportion of $^{51}$Cr release. FIG. 4A shows that CTL expressing chimeric receptors comprising the Src family kinases Lck or Fyn (T), or the Syk family kinase ZAP-70, are incapable of mediating cytolysis against anti-CD16 hybridoma targets. However CTL expressing a kinase chimera based on the Syk protein product were essentially as effective as CTL expressing a chimera composed of CD16 fused in the same manner to the intracellular domain of the T cell receptor zeta chain. The cytolytic activity directed by the CD16/CD7/kinase chimeras could not be ascribed to a nonspecific release of cyototoxic granules because cosedimentation of an irrelevant chromium-laden target with the kinase-armed CTL did not result in detectable release of labeled chromium (FIG. 4B).

Figure 5A:
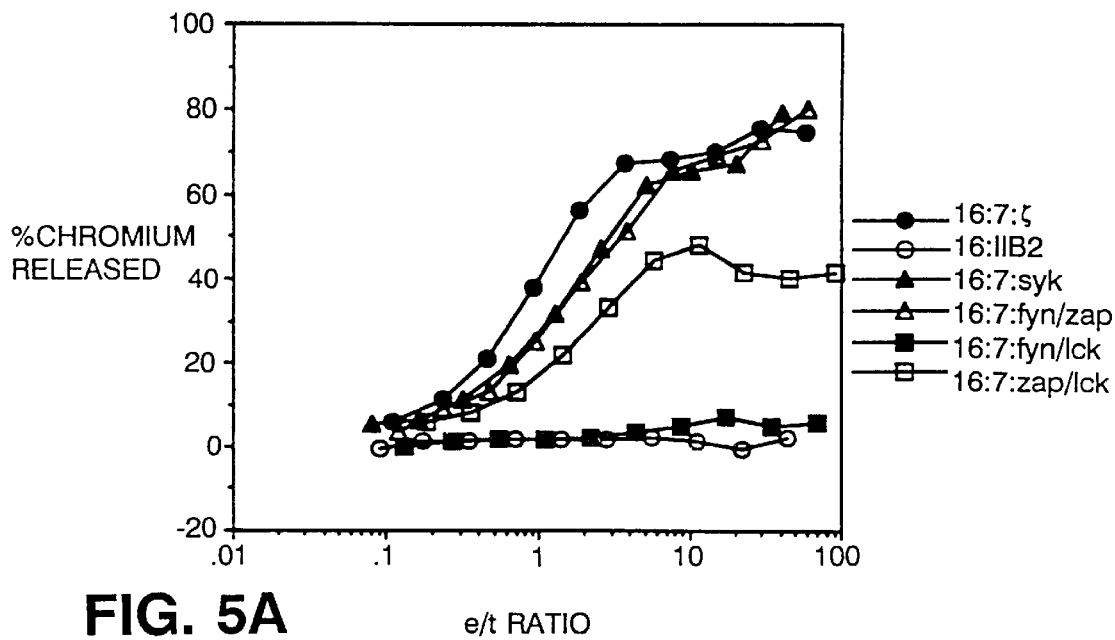
FIGS. 5A, 5B, and 5C show that coexpression of ZAP-70 and Fyn or Lck allows induction of cytolysis and reduces latency for the calcium response. CTL were coinfected with vaccinia recombinants expressing the indicated chimeras and analyzed for cytolytic potential or calcium mobilization. The efficacy of the chimeras is underestimated by this analysis since the fraction of cells expressing both chimeras was not independently measured (the fraction of cells expressing at least one chimera was used to normalize activity).
Figure 5B:
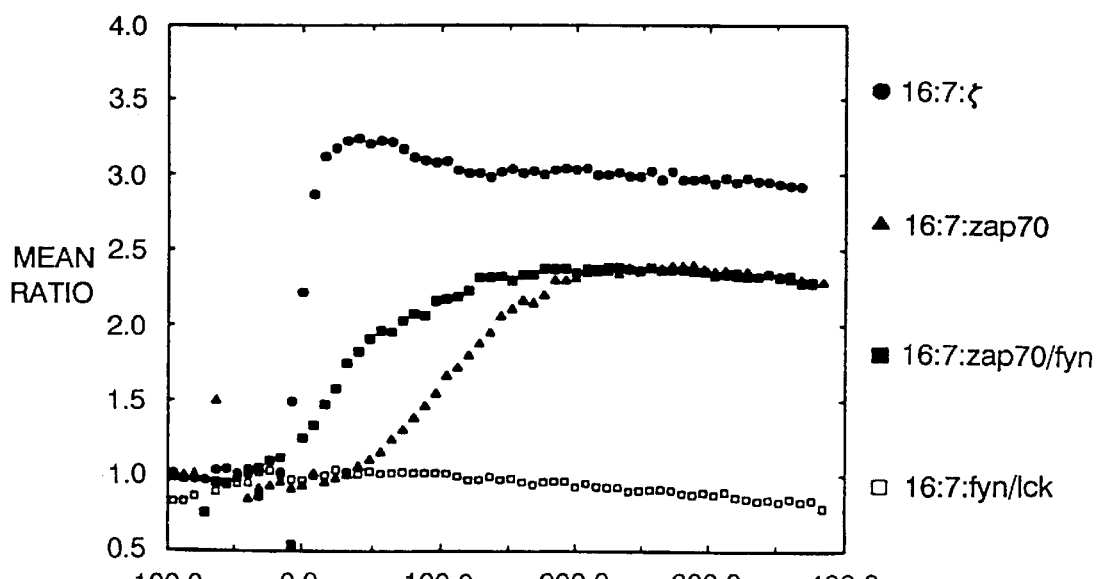
Figure 5C:
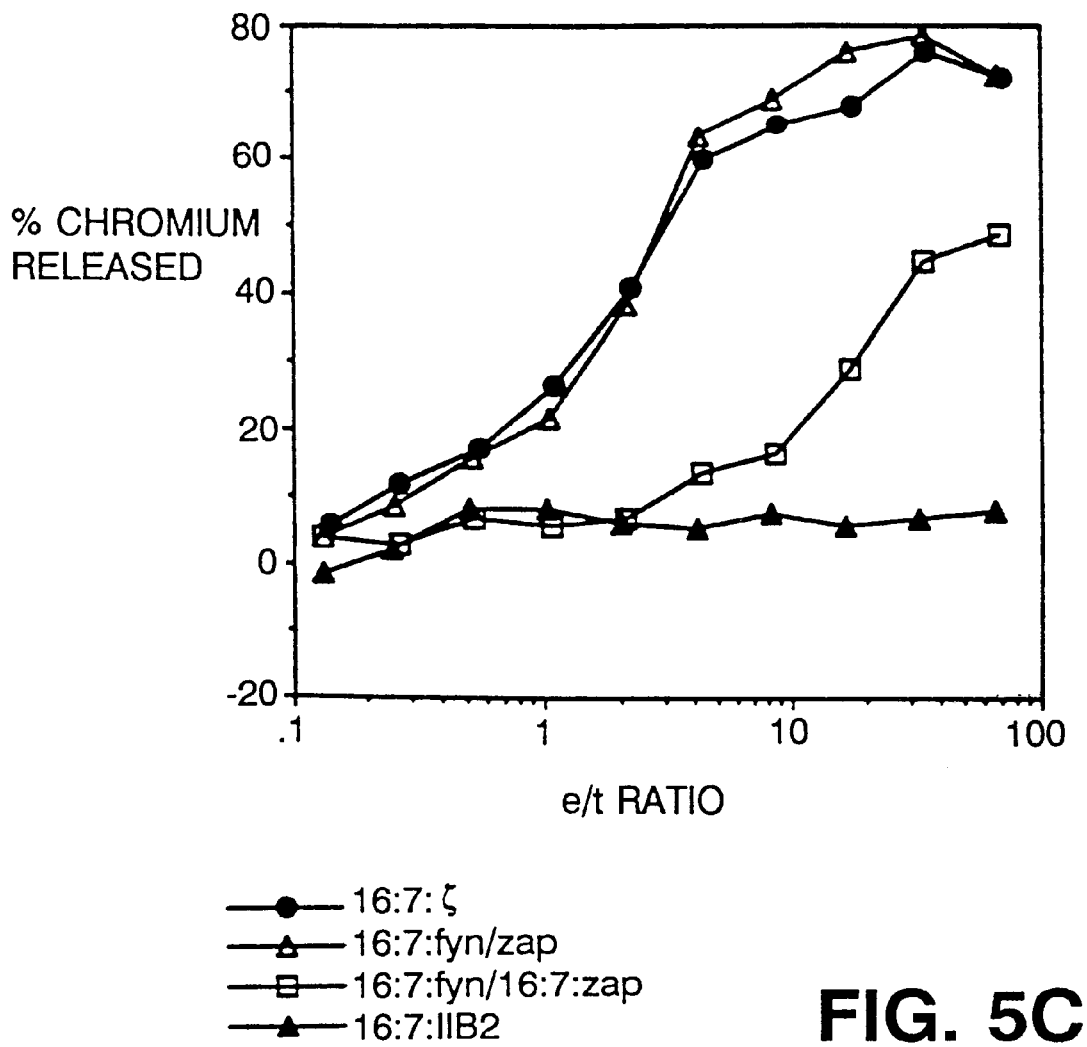

The disparity between Syk and ZAP-70 activities in the cytolysis assay was unexpected in light of the similar activities of the two chimeras in the calcium response assay. In light of the demonstration that coexpression of nonchimeric ZAP-70 and Src-family kinases led to activation in COS cells (Chan et al., 1992, Cell 71:649–662), we undertook an evaluation of the relative potential of pairs of kinase chimeras to effect cytolysis. CTL effectors were coinfected with recombinant vaccinia viruses encoding ZAP-70 and Lck chimeras, ZAP-70 and Fyn (T) chimeras, or Lck and Fyn (T) chimeras. FIG. 5A shows that the coexpression of ZAP-70 and Fyn (T) chimeras, or ZAP-70 and Lck chimeras, endowed CTL with an activity essentially equipotent with that of CTL expressing CD16/CD7/Syk kinase chimeras alone, an activity in turn as potent as that displayed by CD16/CD7/zeta chimeras. Coexpression of Lck and Fyn(T) chimeras did not allow significant cytolytic potential to be redirected against anti-CD16 target cells (FIG. 5A). Evaluation of the calcium mobilization potential of cells coinfected with pairs of kinase fusion proteins showed that coexpression of ZAP-70 and Src family kinase chimeras increased the rapidity with which calcium was mobilized in response to receptor crosslinking and that coexpression of Lck and Fyn(T) chimeras did not result in a significant accumulation of free intracellular calcium (FIG. 5B). To further explore the role of the Fyn chimera in the activation response induced by coaggregation, we prepared a Fyn chimera consisting of the extracellular and transmembrane domains of CD4 fused to Fyn in a manner similar to that of the CD16 chimeras. FIG. 5C shows that the effectiveness of this chimera in there directed cytolysis assay is ten to twenty fold lower than that of the comparable CD16 chimera, suggesting that physical association of the chimeric kinases is important for activation. However the cytolytic activity of cells expressing the two chimeras is significantly greater than would be observed for cells expressing ZAP-70 chimera alone. Because of the relatively high level of kinase expression in this system, it cannot be excluded that the residual activity reflects spontaneous random association of the CD4/Fyn chimera with CD16/ZAP-70.

Figure 6A:
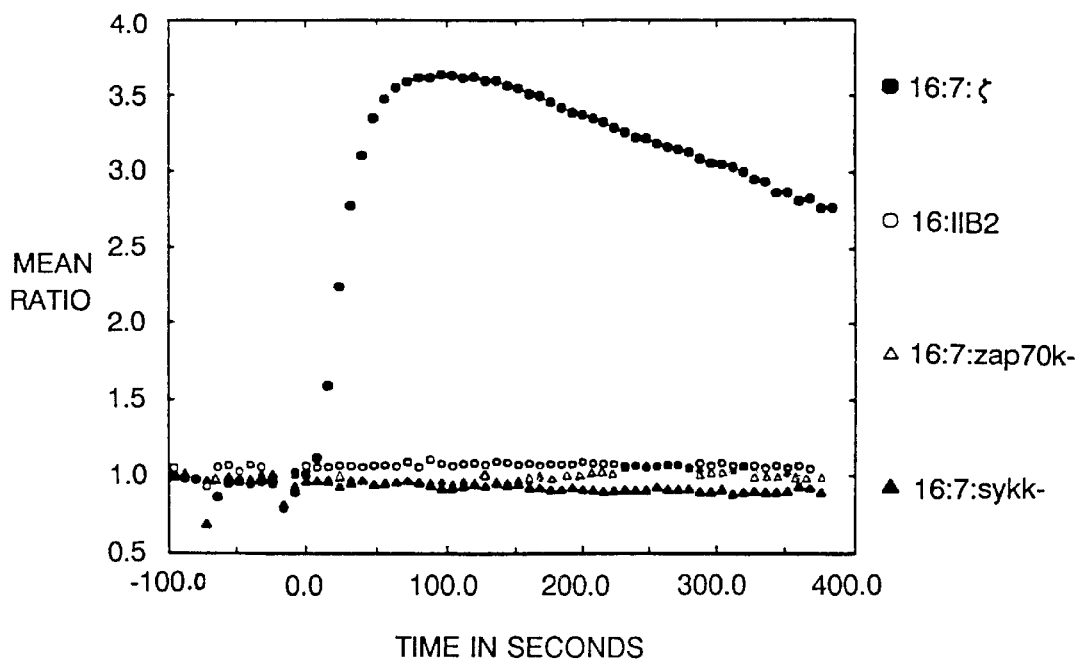
FIGS. 6A and 6B show that chimeras bearing kinase deletions or point mutations are ineffective in calcium mobilization and redirected cytolysis. Kinase negative fusion protein variants were constructed by deletion (in the case of Syk) or point mutation (in the case of ZAP-70) and tested for calcium response and cytolysis.
Figure 6B:
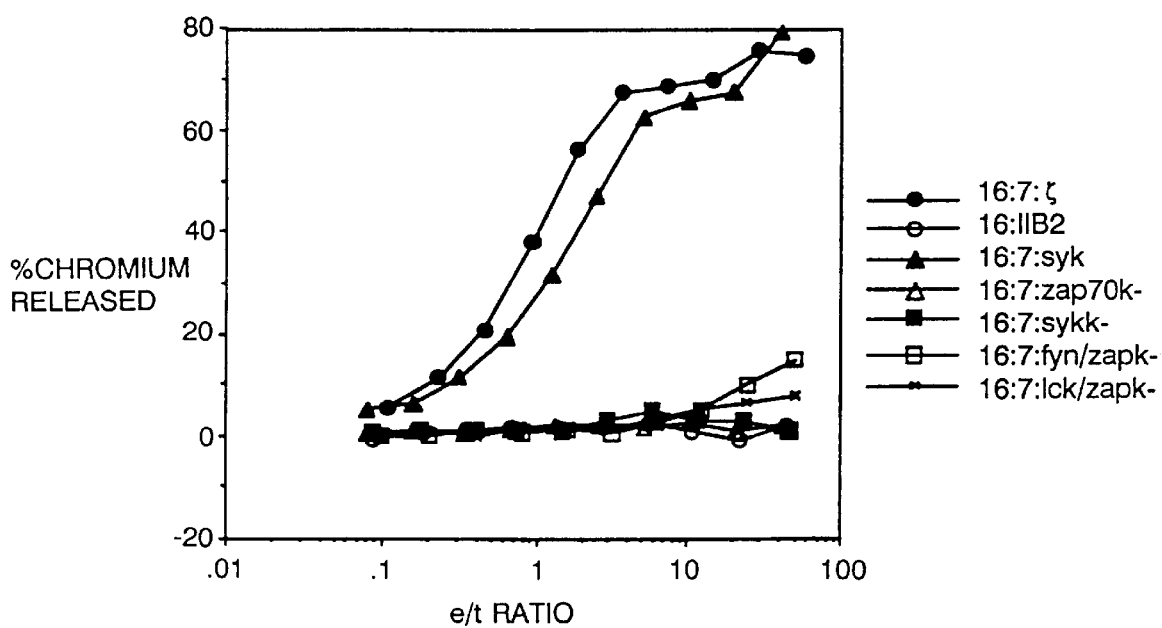

To establish that the activation seen in both calcium response and cytolysis assays was directly attributable to the relevant kinase activity and not to passive association of the kinases with existing signal transduction elements whose indirect aggregation then initiated the activation response, we created kinase negative variants of both the porcine Syk and human ZAP-70 receptor chimeras. FIG. 6 shows that receptor chimeras lacking either substantially all of the kinase domain (in the case of Syk) or bearing a point mutation abrogating phosphotransferase activity (in the case of ZAP-70) lacked in vitro kinase activity and were incapable of mediating calcium mobilization following crosslinking, or of mediating receptor redirected cytolysis.

Figure 7B:
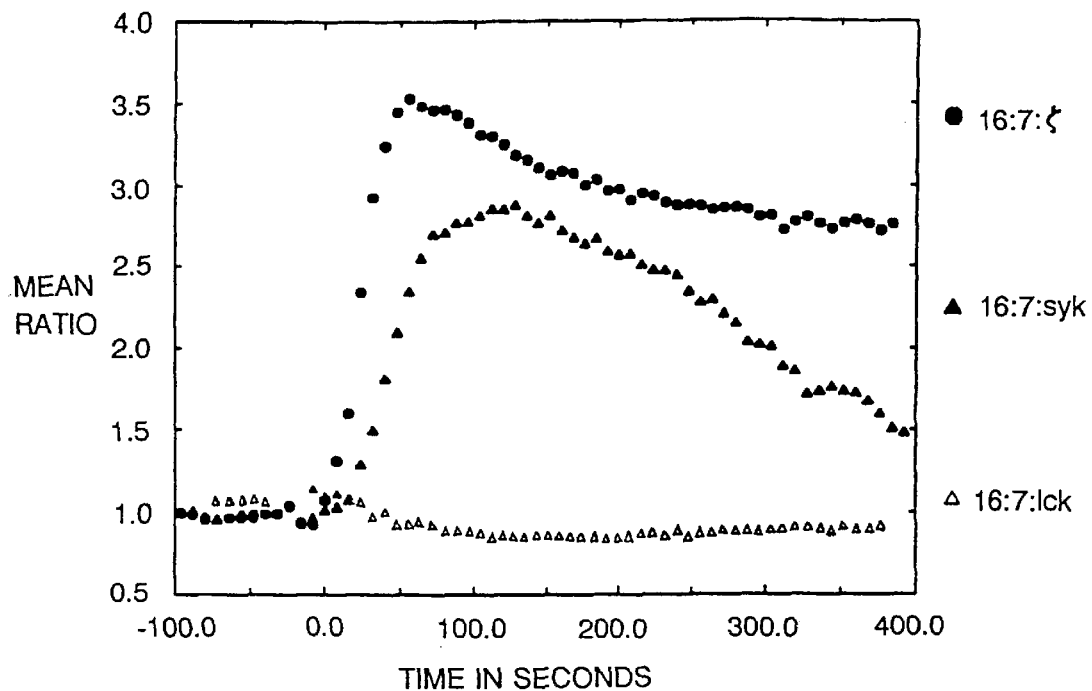
Figure 7C:
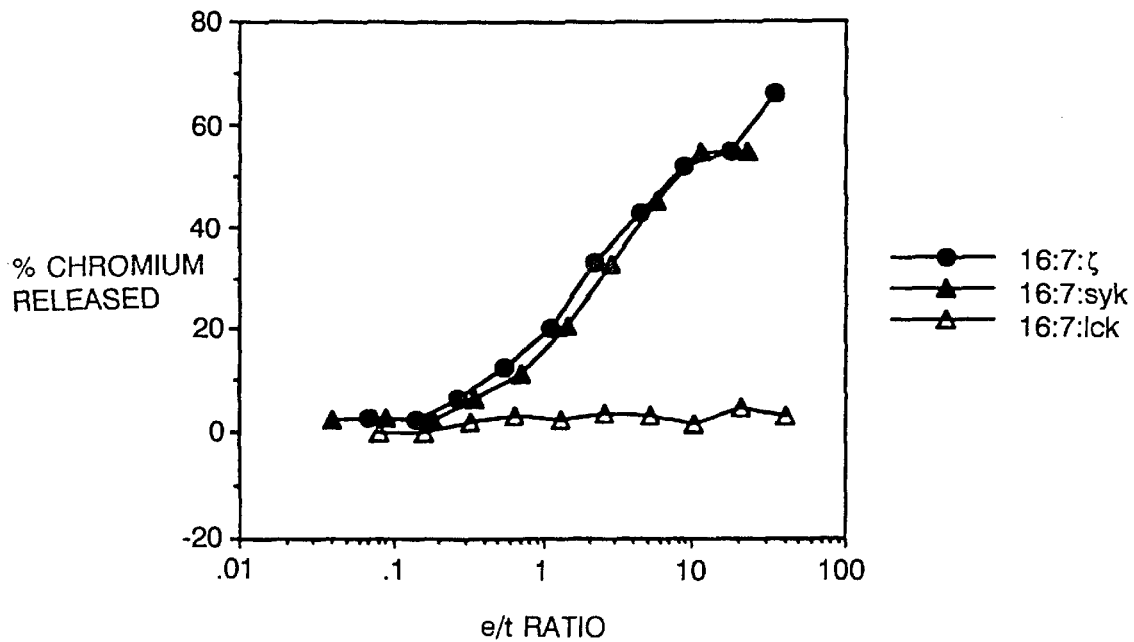

Because the interaction of porcine Syk with the human cellular apparatus might not be identical to the interaction of human Syk, we also constructed similar protein chimeras based on human Syk, after isolating human Syk sequences by PCR with primers corresponding to the amino and carboxyl termini of the porcine protein sequence. FIG. 7A shows that pig and human Syk are strikingly similar proteins, as suggested by analysis of PCR products corresponding to portions of the kinase and second SH2 domains (Chan et al., 1992, Cell 71:649–662). Consonant with this, human Syk chimeric receptor proteins behaved essentially identically to the porcine constructs in calcium release and cytolysis assays (FIGS. 7B and 7C).

Figure 8:
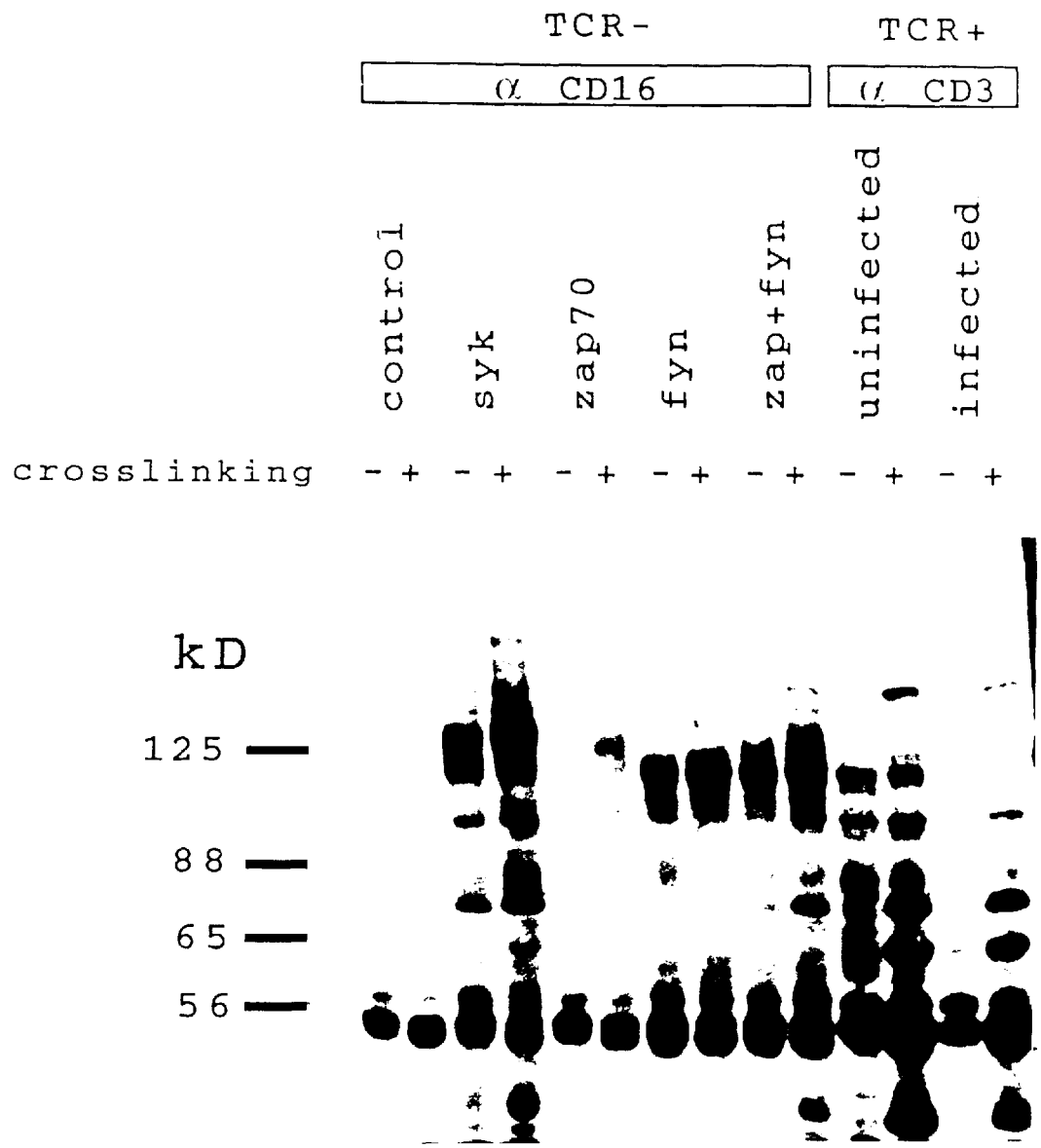
FIG. 8 shows changes in tyrosine phosphorylation pattern following crosslinking of chimeric kinases. T cell antigen receptor-negative Jurkat cells expressing the indicated chimeras or pairs of chimeras were treated with anti-CD16 and goat anti-mouse IgG second antibody and then lysed, fractionated on a polyacrylamide gel, transferred to nitrocellulose and probed with anti-phosphotyrosine antibody. Lanes marked '+' represent extracts from cells subjected to crosslinking, while those marked '–' were lysed directly without prior exposure to secondary antibody. Control lanes were created by similar treatment of TCR-negative cells expressing a CD16/7 fusion protein which did not contain an intracellular domain. For comparison, the effects of anti-CD3 treatment of TCR-positive Jurkat cells (with or without wild type vaccinia virus infection) are shown at right. The prominent bands in the vicinity of 100 kD on the left part of this panel correspond to the expected molecular masses of the kinase chimeras.

To establish whether aggregation of the chimeric tyrosine kinases results in a significant change in the abundance of phosphotyrosine proteins, T cell receptor negative cells were infected with vaccinia recombinants encoding the chimeric kinases. The extracellular domains of the chimeras were crosslinked with antibodies, and total cellular lysates of the activated cells were fractionated by electrophoresis, transferred to membranes and analyzed with an antibody recognizing phosphotyrosine. Lysates were prepared by disruption of cells in nonionic detergents in the presence of vanadate with or without EDTA, or by lysis in the presence of sodium dodecyl sulfate, followed by sonication to shear the liberated DNA. The pattern of phosphotyrosine proteins was different in each case and lysates prepared with vanadate but without EDTA showed additional species not present in lysates prepared in SDS alone, suggesting that EDTA may inhibit the postlysis action of tyrosine kinases as well as phosphatases. The use of direct lysis in SDS was found to lead to more reproducible patterns of protein tyrosine phosphorylation than lysis with nonionic detergents in the presence of EDTA and vanadate. FIG. 8 shows that aggregation of chimeras bearing Syk, ZAP-70, or Fyn plus ZAP-70 results in the appearance or increased phosphorylation of several protein species comigrating with proteins which show increased phosphorylation following antigen receptor crosslinking. In particular, the pattern of bands induced by Syk chimera clustering is very similar to the pattern induced by anti-CD3 antibody in T cell receptor-positive cells (FIG. 8). Among these is an approximately 150 kD protein induced by aggregation of Syk chimera, but also induced by coaggregation of Fyn and ZAP-70 chimeras. In preliminary experiments this phosphoprotein was observed to comigrate with phospholipase C-γ (data not shown).

Figure 9:
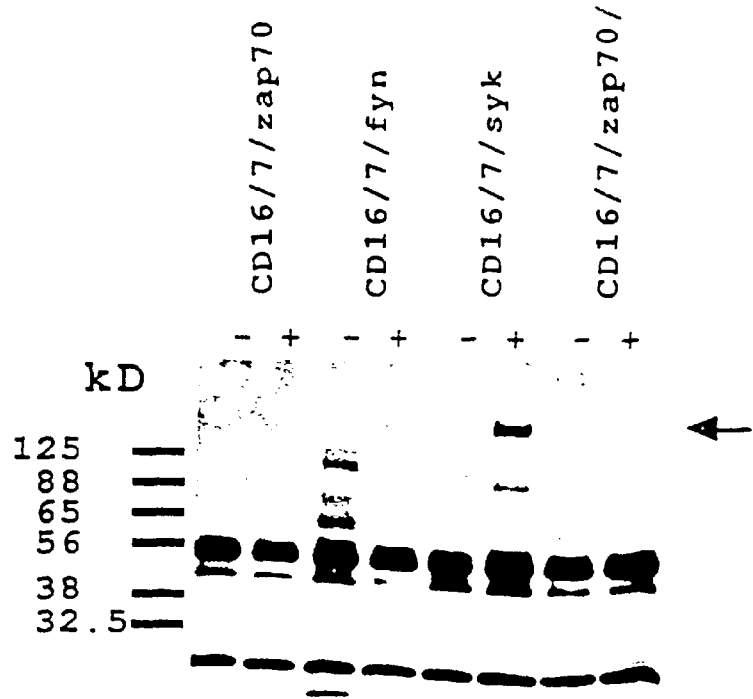
FIG. 9 shows tyrosine phosphorylation of phospholipase C-γ1 following aggregation of chimeras. PLC-γ1 was immunoprecipitated from cells subjected to antibody crosslinking and the immunoprecipitates were fractionated on gels, transferred to nitrocellulose, and probed with anti-phosphotyrosine antibody. A substantial increase in phosphorylated PLC-γ1 was seen following aggregation of Syk chimeras, whereas a more limited but easily detectable increase is seen following coaggregation of Fyn and ZAP-70 chimeras.

To establish the effects of kinase chimera clustering on PLC-γ directly, we crosslinked chimeras, precipitated PLC-γ with a mixture of monoclonal antibodies, and analyzed the resulting immunoprecipitates for the presence of phosphotyrosyl proteins. FIG. 9 shows that clustering of Syk results; in a substantial increase in the tyrosine phosphate content of PLC-γ, while cocrosslinking of Fyn plus ZAP-70 chimeras results in a less dramatic but easily detectable increase in tyrosine phosphate. Cells expressing Fyn chimera alone showed a modest basal phosphorylation of PLC-γ which did not increase following receptor aggregation (FIG. 9). Whether the same tyrosine residues are phosphorylated by Syk, Fyn, or ZAP-70 plus Fyn, is presently unknown. Because cells expressing Fyn chimera showed neither resting nor induced calcium mobilization, the phosphotyrosine signal seen in these cells may represent utilization of other sites on PLC-γ than those which mediate phospholipase activation.

Figure 10A:
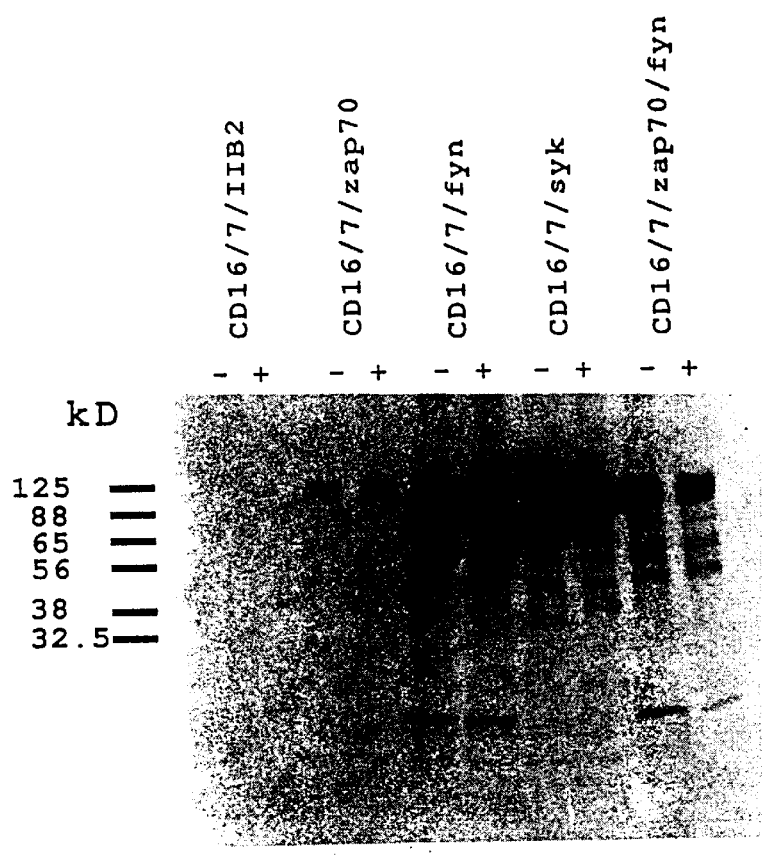
FIGS. 10A and 10B show in vitro kinase assays. Cells expressing chimeric kinases were subjected to antibody-mediated chimera crosslinking, after which the kinases were immunoprecipitated and the immunoprecipitates evaluated for phosphorylation of endogenous substrate.
Figure 10B:
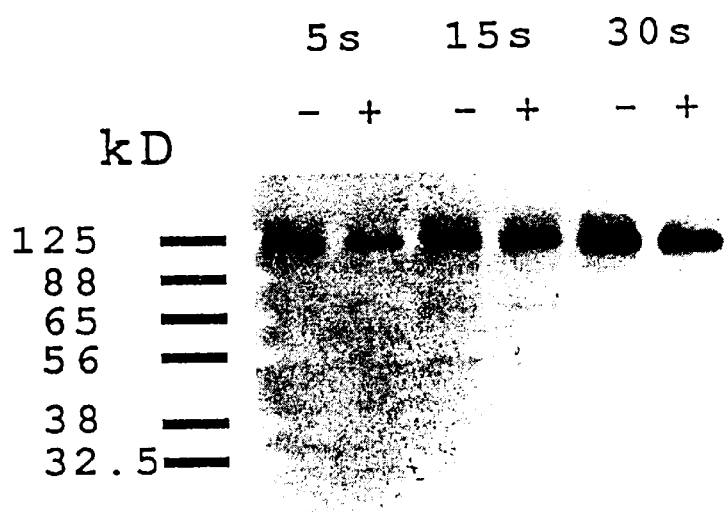

In a preliminary attempt to account for the changes in phosphotyrosine pattern we evaluated the activity of the various kinases following clustering in an in vitro autophosphorylation assay. Chimeras were aggregated, immunoprecipitated, and evaluated for their ability to incorporate phosphate label into the protein species present in the immunoprecipitate. FIG. 10A shows that under these conditions no increase in kinase activity was detected following crosslinking when the kinase assay was carried out for ten minutes. Although incorporation of labeled phosphate continues to increase for up to 30 minutes in this assay, it is unclear what factors limit activity; in particular the observed kinetics may be dominated by the rate of dissociation of the immune complexes, allowing kinase diffusion to unutilized substrate. In an attempt to control for this effect, as well as to maximize the sensitivity of the assay, we also evaluated Syk kinase activity with or without prior crosslinking over a very brief time course from 5 to 30 seconds; however here too there was no significant increase in kinase activity (FIG. 10B). Although at present we cannot exclude the possibility that an increase in activity would be demonstrable with an appropriate substrate, an aggregation-induced increase in Syk chimera activity was also not observed when an exogenous peptide substrate (a Y 19 K substitution of cdc 2 residues 6–20) was used to measure kinase activity.

Possible Mechanisms

The mechanism by which a simple physical stimulus, receptor aggregation, results in the transmission of a distinctive chemical signal to immune system cells remains unknown. Previous studies have established that Src-family kinases can be found associated with many of the important aggregation-activated receptors of the immune system, and that crosslinking of such receptors frequently leads to increased kinase activity. More recently, the related Syk and ZAP-70 kinases have been found to associate either stably (in the case of Syk) or transiently (in the case of ZAP-70) with the B and T cell antigen receptors, respectively, and at least in the case of Syk, receptor crosslinking has been reported to result in increased kinase activity.

In this work we have shown that aggregation of Syk family kinases, but not the Src family kinases Lck or Fyn, leads to a calcium response in cells lacking T cell receptor. The response appears not to be due to an indirect association with other T cell receptor or signal transduction components because kinase negative mutants can not induce the calcium response. Aggregation of chimeras containing the Syk kinase is sufficient to allow induction of specific cytolysis, while induction of similar cytolysis by ZAP-70 chimera requires the additional participation of a Src family kinase. At present it is unclear which of the Syk family kinases is likely to play a more important role in T cell activation: both ZAP-70 and Syk are expressed in T cells, including the cell lines used in this study, and at least one responsive human T cell line contains Syk but not ZAP-70 as judged by specific PCR amplification products. The pattern of increased protein tyrosine phosphorylation seen following Syk chimera clustering is very similar to the pattern seen after crosslinking of the T cell antigen receptor.

One simple model for activation of immune system cells by nonreceptor tyrosine kinases invokes a receptor-associated kinase whose aggregation leads to activation either by physical association (e.g., by forming active kinase dimers) or by mutual enzymatic action (e.g., crossphosphorylation); the activated enzyme then acts on key intracellular substrates required for calcium mobilization and inositolphosphate synthesis. Support for this sequence of events can be found in studies reporting increases in receptor-associated kinase activity following receptor crosslinking (e.g., Bolen et al., 1991, Adv. Cancer Res. 57:103–149; Burkhardt et al., 1991, Proc. Natl. Acad.

Sci. USA 88:7410–7414; Eiseman and Bolen, 1992, Nature 355:78–80; Hutchcroft et al., 1992, Proc. Natl. Acad. Sci. USA 89:9107–91111/J. Biol. Chem. 267:8613–8619; Tsygankov et al., 1992, J. Biol. Chem. 267:18259–18262; Wong et al., 1992, Oncogene 7:2407–2415). However the reported changes in kinase activity are in most cases modest, and contrast with the dramatic changes in phosphotyrosyl protein pattern seen in vivo. Because it is difficult to unambiguously rule out activation by weak allosteric interactions using in vitro kinase assays as a tool, we cannot at this point make a definitive statement about the relative importance of kinase activation in the initiation of signal transduction. But the data presented here suggest that aggregation-induced repartitioning of enzyme and substrate may be an important factor in directing an existing activity toward the appropriate physiological target.

Aggregation of chimeras based on Syk family kinases led to a calcium response which was slightly delayed but similar in amplitude to the response seen following aggregation of zeta receptor chimeras in cells lacking endogenous T cell receptor. A more profound delay in the appearance of free calcium ion was observed following ZAP-70 chimera crosslinking, and this delay could be substantially abolished by cocrosslinking ZAP-70 and Fyn chimeras. At present the explanation for the observed latency is unclear. Because cocrosslinking accelerated calcium mobilization, it is tempting to ascribe the delay to the relative inefficacy of ZAP-70 for aggregation-mediated autoactivation. But other factors may be equally important, and the tethering of ZAP and Syk kinases at the cell surface may actually be an impediment to activation when compared to the normal process; for example if in the normal course of events Syk family kinases are transiently recruited to clustered receptors, activated and then released to diffuse to their substrates, the permanent linkage of the kinase domain to the plasma membrane could be restrictive by hindering access to substrate and/or limiting signal amplification due to the inability of the chimeric receptors to function as a kind of catalytic center for kinase activation.

A second peculiarity of the calcium response was the finding that T cell receptor positive cells expressing chimeras based on human or porcine Syk showed a high baseline concentration of free calcium ion, suggesting that calcium release had been spontaneously triggered. A similar finding was not observed in receptor negative cells. This result runs counter to a general trend we have observed, in which T cell receptor negative mutants of human T cell tumor lines typically are hyperresponsive to exogenously introduced trigger molecules. To account for the apparent requirement for T cell receptor in the spontaneous activation process, we propose two possible and related explanations. One is that chimeric Syk kinase may act constitutively on T cell receptor intracellular domains to create phosphotyrosine targets for the SH2 domains of the receptor chimera, leading to intracellular aggregation through a multivalent T cell receptor bridge, in turn promoting kinase activation. Another possibility is that the T cell receptor negative cell line may have lower levels of a membrane associated kinase required for activation of Syk, either because a global regulatory circuit results in decreased de novo synthesis of the hypothetical kinase, or because the absence of antigen receptor results in a disregulated intracellular trafficking.

In B cells, the Syk kinase has been reported to be constitutively associated with the intracellular elements of the IgM antigen receptor (Hutchcroft et al., 1992, Proc. Natl. Acad. Sci. USA 89:9107–91111; Hutchcroft et al., 1992, J. Biol. Chem. 267:8613–8619). The exact mechanism of this association is unclear, but one possibility is that phosphotyrosine is not required for interaction of Syk SH2 domains with the tyrosine trigger motif present in the cytoplasmic domain of the mb-1 and B 29 receptor chains. A partial precedent for this suggestion is the report that the Philadelphia chromosome breakpoint cluster region gene product BCR binds to a variety of SH2 domains in a phosphotyrosine independent manner (Pendergast et al., 1991, Cell 66:161–171; Muller et al., 1992, Mol. Cell. Biol. 12:5087–5093). In this case, though, it appears likely that phosphoserine and/or phosphothreonine residues play a critical role in the interaction. Alternatively, Syk may associate with IgM receptor intracellular motifs through the unique region located between the Syk SH2 elements and the catalytic domain. A third possibility is that only a very small amount of tyrosine phosphorylated peptide is necessary to recruit functionally important levels of Syk to the inner face of the plasma membrane, and this low level of tyrosine phosphate has thus far escaped detection.

Although in B cells the requirement for a Src family kinase in activation has not been definitively established, in T cells two kinases, Lck and Fyn (T) have been shown by somatic or organismic genetics to play important roles (Appleby et al., 1992, Cell 70:751–763; Karnitz et al., 1992, Mol. Cell. Biol. 12:4521–4530; Stein et al., 1992, Cell 70:741–750; Straus and Weiss, 1992, Cell 70:585–593). At present we cannot conclusively establish whether the action of these kinases normally precedes or follows the action of the Syk family kinases. One hypothesis accounting for the action of ZAP-70 in T cell activation invokes a receptor-associated Src family kinase whose aggregation permits a transitory phosphorylation of receptor chains in turn leading to association of ZAP-70 and subsequent cellular activation. The initial phosphorylation of receptor chains proposed in this model must be distinguished from the stable phosphorylation of zeta seen at longer times following receptor crosslinking.

In murine T cells a small proportion of T cell receptor complexes contain a zeta-related molecule called eta (Baniyash et al., 1988, J. Biol. Chem. 263:9874–9878) which represents an alternatively spliced form (Clayton et al., 1991, Proc. Natl. Acad. Sci. USA 88:5202–5206). Eta differs from zeta at the carboxyl terminus, and lacks the most distal of the six tyrosines found in murine zeta (Jin et al., 1990, Proc. Natl. Acad. Sci. USA 87:3319–3323). Although the phosphorylation of the zeta chain of murine TCR zeta-zeta isoforms can readily be detected following antibody-mediated receptor crosslinking, under similar circumstances the TCR eta chain is not detectably phosphorylated (Bauer et al., 1991, Proc. Natl. Acad. Sci. USA 88:3842–3846). Stable phosphorylation of the zeta chain appears to require two closely apposed zeta chains since TCR isoforms bearing zeta-eta heterodimers are not phosphorylated following receptor crosslinking (Bauer et al., 1991, Proc. Natl. Acad. Sci. USA 88:3842–3846). Despite the differences in phosphorylation, cell lines comprising TCR isoforms consisting solely of eta homodimers are functionally indistinguishable from cell lines bearing only zeta homodimers (Bauer et al., 1991, Proc. Natl. Acad. Sci. USA 88:3842–3846). Thus phosphorylation of zeta, as observed 30 minutes after antibody mediated receptor aggregation, does not correlate with activation. In a separate study, examination of the time course of accumulation of phosphotyrosine phosphoproteins following TCR aggregation has shown that the earliest observable species are two proteins of mass 135 and 100 kD, whose phosphorylation is first detectable at five and fifteen seconds after crosslinking, respectively, and whose half maximal phosphorylation, in both cases at approximately 30 seconds, precedes the times of half maximal calcium mobilization and inositol phosphate formation (June et al., 1990, Proc. Natl. Acad. Sci. USA 87:7722–7726; June et al., 1990, J. Immunol. 144:1591–1599). By contrast, the rate of phosphorylation of zeta is substantially slower, leading to half maximal substitution at approximately three to five minutes post-stimulation, well after calcium accumulation and liberation of inositol phosphates are observed (June et al., 1990, Proc. Natl. Acad. Sci. USA 87:7722–7726; June et al., 1990, J. Immunol. 144:1591–1599).

Thus if the two step model is correct, the tyrosine phosphorylation necessary to recruit ZAP-70 to the inner face of the plasma membrane must be a more rapid, presumably transitory, event than observed in the studies above. Recently it has been suggested that tyrosine phosphorylation with an appropriately fast (ca. fifteen second) onset can be detected on both zeta and CD3 epsilon chains following receptor crosslinking (Wange et al., 1992, J. Biol. Chem. 267:11685–11688), and that a 70 kD protein bearing tyrosine phosphate can be found associated with both zeta and epsilon chains. It is not presently clear whether a stable association with phosphorylated receptor chains is a prerequisite for successful T cell activation.

As a general assertion, though, the results reported here suggest that Syk family kinases act more directly on the effector apparatus of T cells than Src family kinases. An increasing body of evidence suggests that Src family kinases can associate with a number of cell surface molecules which are not members of the antigen/Fc receptor family, including CD2 (Bell et al., 1992, Mol. Cell. Biol. 12:5548–5554), CD23 (Sugie et al., 1991, Proc. Natl. Acad. Sci. USA 88:9132–9135), CD36 (Huang et al., 1992, J. Biol. Chem. 267:5467–5473), IL-2 receptor beta chain (Hatakeyama et al., 1991, Science 252:1523–1528) and various phosphatidylinositol anchored proteins (Stefanova et al., 1991, Science 254:1016–1019; Thomas and Samelson, 1992, J. Biol. Chem. 267:12317–12322), some of which are known to require the additional presence of the antigen receptor to promote activation in T cells. A simple explanation for the latter requirement maybe that the trigger motifs on the antigen receptor act as substrates for Src family kinases, allowing the subsequent docking of Syk family kinases, followed perhaps by some modifying event promoting their activation. Given the difficulty of establishing a causal chain of phosphorylation and activation it may also be that the trigger motifs have only a transitory role, to act as a kind of catalytic center for the recruitment, activation, and release of effector kinases.

Src family kinases are broadly distributed throughout nonhematopoietic lineages, and recent studies using Fyn negative mice have shown a role for Fyn in the sustenance of long term potentiation, the phenomenon of facilitated synaptic transmission thought to underlie the initial consolidation of associative memory (Grant et al., 1992, Science 258:1903–1910). If similar activation pathways are mediated by Src family kinases in other cell types, Syk family kinases may also prove to be more extensively distributed throughout the extrahematopoietic compartments.

Experimental Methods
Construction of Chimeras

The entire coding regions of the human Lck (Koga et al., 1986, Eur. J. Immunol. 16:1643–1646), murine Fyn (T) (Cooke and Perlmutter, 1989, New. Biol. 1:66–74), porcine Syk (Taniguchi et al., 1991, J. Biol. Chem. 266:15790–15796) and human ZAP-70 (Chan et al., 1992, Cell 71:649–662) kinases were attached to the intracellular domain of a chimeric transmembrane protein consisting of the CD16 extracellular domain joined to a short 'stalk' segment and transmembrane domain of CD7. The CD7 intracellular domain was truncated at the stop transfer sequence by addition of an Mlu site. The various kinases were adapted with an Mlu site in the appropriate reading frame to allow a tripartite fusion protein to be expressed. The pig Syk sequence was obtained by reverse transcription and PCR of total pig lymphocyte RNA using primers bearing appropriate restriction sites. ZAP-70 sequences were similarly obtained by PCR from a human T cell cDNA library. Several isolates were sequenced in parallel and a mutation-free coding sequence was derived for each kinase by restriction fragment interchange. The resulting coding sequences were inserted into a vaccinia virus expression vector downstream from the CD16/CD7 sequences. Human Syk was isolated from a natural killer cell cDNA library and from a Daudi cell library using primers corresponding to the ends of the porcine sequence. The forward primer bore the sequence atg gca gac agt gcc aac cac ttg ccc ttc ttc t and the reverse primer bore the sequence cgc ggg gcg gcc gct tta att cac cac gtc gta gta gta. After initial amplification revealed the presence of bands of the expected size a reamplification (10 cycles) was performed using an extension primer at the 5' end having the sequence cgc ggg acg cgt acc atg gca gac agt gcc aac, allowing the fragment to be ligated to an Mlu I-cut vector.

Calcium Mobilization Analysis

Flow cytometric and bulk spectrophotometric analyses were conducted on cells expressing recombinant kinases using the calcium sensitive fluorophore Indo-1 as previously described (Romeo and Seed, 1991, Cell 64:1037–1046; Romeo et al., 1992, Cell 68:889–897). Briefly, cells of the Jurkat mutant subline JRT 3.T 3.5 (Weiss and Stobo, 1984, J. Exp. Med. 160:1284–1299) were infected with recombinant vaccinia viruses for one hour in serum free IMDM at an moi of 10 and incubated for three to nine hours in IMDM, 10% FBS. Cells were collected by centrifugation and resuspended at $3\times10^6$/ml in complete medium containing 1 mM Indo-1 acetomethoxyester (Grynkiewicz et al., 1985, J. Biol. Chem. 260:3440–3450) (Molecular Probes, Eugene, Oreg.) and incubated at 37° C. for 45 minutes. The Indo-1 loaded cells were pelleted and resuspended at $1\times10^6$/ml in serum free IMDM and stored at room temperature in the dark. Cells were analyzed for free calcium ion by simultaneous measurement of the violet and blue fluorescence emission by flow cytometry (Rabinovitch et al., 1986, J. Immunol. 137:952–961). To initiate calcium flux, either unconjugated 3G8 (anti-CD16) monoclonal antibody (at 1 $\mu$g/ml) was added to the cell suspension followed by 10 $\mu$g/ml of phycoerythrin (PE)-conjugated Fab 02 goat anti-mouse IgG at time 0, or a PE-conjugated anti-CD4 antibody (Leu-3a, Becton Dickinson) was added, followed by unconjugated second antibody. Histograms of the violet/blue emission ratio were collected from the PE positive (infected) cell population, which typically represented 40–80% of the cells. The violet/blue emission ratio prior to the addition of antibody was used to establish the normalized initial ratio, set equal to unity.

Lymphocyte Cytolysis Assay

A CD8+ CD4− HLA B44 restricted cytolytic line (WH3) was maintained in IMDM, 10% human serum with 100 U/ml of IL-2 and was periodically stimulated with irradiated (3000 rad) mononuclear cells having the HLA B44 haplotype. Cells were grown for at least 10 days following stimulation before use in cytotoxicity assays. The cells were infected with recombinant vaccinia at a multiplicity of infection of at least 10 for one hour in serum free medium, followed by incubation in complete medium for three hours. Cells were harvested by centrifugation and resuspended at a density of $1\times10^7$/ml. 100 µl were added to each well of a U-bottom microtiter plate containing 100 µl/well of complete medium. Cells were diluted in two-fold serial steps. Two wells for each sample did not contain lymphocytes, to allow spontaneous chromium release and total chromium uptake to be measured. An aliquot of $10^6$ 3G8 10-2 target cells (Shen et al., 1989, Mol. Immunol. 26:959–969) or was centrifuged and resuspended in 50 µl of sterile $^{51}$Cr sodium chromate (1 m Ci/ml, DuPont) for one hour at 37° C. with intermittent mixing, then washed three times with PBS. 100 µl of labelled cells resuspended in medium at $10^5$/ml were added to each well. The microtiter plate was spun at 750×g for 1 minute and incubated for 4 hours at 37° C. At the end of the incubation period the cells in each well were resuspended by gentle pipetting, a sample removed to determine the total counts incorporated, and the microtiter plate was spun at 750×g for 1 minute. 100 µl aliquots of supernatant were removed and counted in a gamma rays cintillation counter. The effector to target ratio was corrected for the percent of effector cells infected (usually >70%).

Creation of Mutant Kinase Chimeras

A porcine Syk kinase negative fusion protein variant was created by cleavage of the chimera with Stu I and Not I (the latter lying just 3' to the carboxyl terminus), filling in the Not I site, and ligating the ends together. The resulting sequence joined the first 298 residues of pig Syk to 4 extraneous residues (GPRL) before terminating. A point mutation (K369G) in the ATP binding site of ZAP-70 was created by insertion of a duplex oligonucleotide fragment between the BalI and EarI sites located between nucleotide residues 1319 and 1345 of the top strand of the sequence reported by Chan et al. (1992, Cell 71:649–662). The resulting sequence encoded glycine at residue 369 in place of lysine.

Immunoprecipitation and Kinase Assay

Approximately $2\times10^6$ Hela S3 cells were infected for one hour in serum free DME medium with recombinant vaccinia at a multiplicity of infection of at least ten. 5 hrs after infection the cells were harvested, washed twice with phosphate buffered saline and lysed in 1% Triton X-100, 0.15 M NaCl, 0.02 M HEPES pH 7.3, 5 mM EDTA, 5 mM NaF, 0.2 m MNaVO$_3$, 10 µg/ml leu peptin, 10 µg/ml a protinin and 1 mM PMSF. After a 10 min. incubation on ice, the nuclei were removed by centrifugation and the CD16 fusion proteins immunoprecipitated with antibody BMA209/2 and protein-A sepharose. The fusion protein loaded resin was washed 3 times with lysis buffer followed by a final wash with 20 mM Hepes pH 7.3. To each sample was added 10 µl of kinase buffer (20 mM Hepes pH 7.3, 10 mM MgCl$_2$, 10 mM MnCl$_2$) containing 10 µCi of [γ-$^{32}$P]ATP (>3000 Ci/mmole). The reactions were allowed to incubate at room temperature for 10 min. and terminated by the addition of 20 µl of 2×sample loading buffer (4% SDS, 100 mM Tris pH6.8, 20% glycerol, and 10% β-mercaptoethanol). After the samples were boiled for 3 min., aliquots were run on a 4–15% gradient gel. Kinase assays with a soluble peptide substrate corresponding to positions 6–20 of cdc 2, in which tyr 20 was replaced with lys, were performed according to the manufacturer's recommendations (UBI).

Immunoblot Analysis of Protein Tyrosine Phosphorylation

TCR negative 3.5 cells were infected with recombinant virus stocks (moi of at least 10) for one hour. Cells were subsequently incubated at 37° C. for 8–12 h, centrifuged, washed and resusupended in Iscove's medium without serum at $10^7$ cells per ml. Aliquots of cells were incubated with anti-CD16 mAb (3G8, Medarex or BMA209/2, Behringwerke) at 1 µg antibody per $2-3\times10^6$ cells. Stimulated samples were further incubated with a 3–5 fold excess of an affinity purified anti-mouse IgG 1 antibody (Southern Biotechnology) for 5 min. Cells were subsequently processed according to Secrist, J. P., Burns, L. A., Karnitz, L., Koretzky, G. A., and Abraham, R. T. (J. Biol. Chem. 268,5886–5893, 1993). with slight modifications. Incubations were terminated by adding SDS to a final concentration of 1% and samples were boiled for three minutes. DNA was sheared by sonication for 1 min using a Heat Systems Ultrasonics, Inc., 2×sample buffer was added and aliquots corresponding to $10^5$ to $2.5\times10^5$ cells were separated on polyacrylamide gels and the proteins transferred by semidry electroblotting (Hoefer) onto nitrocellulose (Schleicher and Schuell BA45). Filters were blocked for one hour in Tris Buffered Saline with 0.05% Tween-20 (TBST) containing 1.5% chicken ovalbumin (Sigma), washed in TBST, and transferred into solution containing anti-phosphotyrosine antibody 4G10 (UBI) at a 1:10000 dilution and incubated at 22° for 1–2 h. After TBST washes, filters were incubated in TBST and a 1:5000 dilution of anti-mouse horseradish peroxidase conjugate for 1 h. Phosphorylated protein bands were detected by chemiluminescence (ECL, Amersham). Exposure times varied between 2 s and 5 min.

Construction of Human IgG1:Protein-Tyrosine Kinase Chimeras

Chimeric molecules may be produced which include the extracellular domain of an antibody molecule specific for a target cell and the intracellular domain of a protein-tyrosine kinase (e.g., those kinases described herein). To produce such a molecule, human IgG1 heavy chain sequences are prepared by joining sequences in the $C_H3$ domain to a cDNA fragment derived from the 3' end of the transmembrane form of the antibody mRNA,. The 3' end fragment is obtained by polymerase chain reaction using a tonsil cDNA library as substrate, and oligonucleotides having the sequences:

CGC GGG GTG ACC GTG CCC TCC AGC AGC TTG GGC and

CGC GGG GAT CCG TCG TCC AGA GCC CGT CCA GCT CCC CGT CCT GGG CCT CA, corresponding to the 5' and 3' ends of the desired DNA fragments respectively. The 5' oligo is complementary to a site in the $C_H1$ domain of human IgG1, and the 3' oligo is complementary to a site just 5' of the sequences encoding the membrane spanning domain. The PCR product is digested with BstXI and BamHI and ligated between BstXI and BamHI sites of a semisynthetic IgG1 antibody gene bearing variable and constant regions. Following the insertion of the BstXI to BamHI fragment, the amplified portions of the construct are replaced up to the SmaI site in $C_H3$ by restriction fragment interchange, so that only the portion between the SmaI site and the 3' oligo is derived from the PCR reaction.

To create a human IgG1 chimeric receptor, the heavy chain gene ending in a BamHI site is joined to the kinase intracellular domain of interest by standard techniques. Levels of chimeric receptor expression may be determined by flow cytometry. Increases in expression may be accomplished by coexpression of a plasmid encoding an antibody light chain cDNA.

To create a single transcription unit which would allow both heavy and light chains to be expressed from a single promoter, a plasmid encoding a bicistronic mRNA is created from heavy and light chain coding sequences, and the 5' untranslated portion of the mRNA encoding the 78 kD glucose regulated protein, otherwise known as grp78, or BiP. grp78 sequences are obtained by PCR of human genomic DNA using primers having the sequences:

CGC GGG CGG CCG CGA CGC CGG CCA AGA CAG CAC and

CGC GTT GAC GAG CAG CCA GTT GGG CAG CAG CAG at the 5' and 3' ends respectively. Polymerase chain reactions with these oligos are performed in the presence of 10% dimethyl sulfoxide. The fragment obtained by PCR is digested with NotI and HincII and inserted between NotI and HpaI sites downstream from human IgG1 coding sequences. Sequences encoding a human IgG kappa light chain cDNA are then inserted downstream from the grp78 leader, using the HincII site and another site in the vector. The expression plasmid resulting from these manipulations consists of the semisynthetic heavy chain gene, followed by the grp78 leader sequences, followed by the kappa light chain cDNA sequences, followed by polyadenylation signals derived from an SV40 DNA fragment. We have previously demonstrated that transfection of COS cells with this expression plasmid gave markedly improved expression of heavy chain determinants, compared to transfection of plasmid encoding heavy chain determinants alone.

To create a bicistronic gene comprising a heavy chain/receptor chimera and a light chain, the upstream heavy chain sequences can be replaced by any chimeric heavy chain/receptor gene described herein.

Once constructed, the IgG-tyrosine kinase chimeras may be cloned into an expression vector, introduced into a host cell, and tested by any of the assays described herein (e.g., by calcium mobilization or cytolysis assays).

Construction of CD4 -Tyrosine Kinase Chimeras

Chimeric molecules may be produced which include the extracellular domain of the CD4 molecule and the intracellular domain of a protein-tyrosine kinase (e.g., those kinases described herein). To produce such a molecule, the tyrosine kinase-encoding sequence (for example, cDNA) is isolated (for example, as described above). This sequence is then joined to the extracellular domain of an engineered form of CD4 possessing a BamHI site just upstream of the membrane spanning domain (Aruffo et al., *Proc. Natl. Acad. Sci. USA*, 84:8573–8577 (1987b); Zettlmeissl et al., *DNA Cell Biol.*, 9347–353 (1990)) by standard techniques. To form this fusion protein, a BamHI site may be engineered into the sequence at the appropriate location (again, by standard techniques). The gene fusions are introduced into a vaccinia virus expression plasmid (as described herein), and inserted into the genome of the vaccinia WR strain by homologous recombination and selection for growth in mycophenolic acid (Falkner et al., *J. Virol.*, 62:1849–1854 (1988); Boyle et al., *Gene*, 65:123–128 (1988)). Flow cytometric analysis is used to examine expression by the vaccinia recombinants of the CD4-tyrosine kinase fusion proteins at the cell surface. Immunoprecipitation of cells infected with the vaccinia recombinants is used to confirm the results (as described above).

The efficacy of CD4 chimeras may be tested by any of the calcium mobilization or cytolysis assays described herein. In one particular example, a model target:effector system based on CD4 recognition of the HIV envelope gp120/gp41 complex is created. HeLa cells are infected with recombinant vaccinia viruses expressing gp120/gp41 (Chakrabarti et al., *Nature*, 320:535–537 (1986); Earl et al., *J. Virol.*, 64:2448–2451 (1990)) and labeled with $^{51}$Cr. The labeled cells are incubated with cells from a human allospecific (CD8$^+$, CD4$^-$) cytotoxic T lymphocyte line which has been infected with vaccinia recombinants expressing the CD4-tyrosine kinase chimera, and examined to specific lysis.

To control for the possibility that vaccinia infection might promote artefactual recognition by CTL, similar cytolysis experiments are performed with target cells infected with vaccinia recombinants expressing the phosphatidylinositol linked form of CD16 (CD16$_{Pf}$) and labeled with $^{51}$Cr, and with CTL infected with control recombinants expressing CD16 chimeras.

In another example, neutrophilic granulocytes, which have a very short lifespan ($\approx$4 h) in circulation and are intensely cytolytic, are attractive cells for expression of CD4-tyrosine kinase chimeras. Infection of neutrophils with HIV is not likely to result in virus release, and the abundance of these cells (the most prevalent of the leukocytes) should facilitate host defense. Another attractive possiblity for host cells are mature T cells, a population presently accessible to retroviral engineering (Rosenberg, S. A. *Sci. Am.*, 262:62–69 (1990)). With the aid of recombinant IL-2, T cell populations can be expanded in culture with relative ease, and the expanded populations typically have a limited lifespan when reinfused (Rosenberg et al., *N. Engl. J. Med.*, 323:570–578 (1990)).

Under the appropriate conditions, HIV recognition by cells expressing CD4 chimeras should also provide mitogenic stimuli, allowing the possibility that the armed cell population could respond dynamically to the viral burden. Although we have focused here on the behavior of the fusion proteins in cytolytic T lymphocytes, expression of the chimeras in helper lymphocytes might provide an HIV-mobilized source of cytokines which could counteract the collapse of the helper cell subset in AIDS. Recent description of several schemes for engineering resistance to infection at steps other than virus penetration (Friedman et al., *Nature*, 335:452–454 (1988); Green et al., *Cell*, 58:215–223 (1989); Malim et al., *Cell*, 58:205–214 (1989); Trono et al., *Cell*, 59:113–120 (1989); Buonocore et al., *Nature*, 345:625–628 (1990)) suggests that cells bearing CD4 chimeras could be designed to thwart virus production by expression of appropriate agents having an intracellular site of action.

The ability to transmit signals to T lymphocytes through autonomous chimeras also provides the ability for the regulation of retrovirally engineered lymphocytes in vivo. Crosslinking stimuli, mediated for example by specific IgM antibodies engineered to remove complement-binding domains, may allow such lymphocytes to increase in number in situ, while treatment with similar specific IgG antibodies (for example recognizing an amino acid variation engineered into the chimeric chain) could selectively deplete the engineered population. We have previously determined that anti-CD4 IgM antibodies do not require additional crosslinking to mobilize calcium in Jurkat cells expressing CD4:ζ chimeras. The ability to regulate cell populations without recourse to repeated extracorporeal amplification may substantially extend the range and efficacy of current uses proposed for genetically engineered T cells.

OTHER EMBODIMENTS

To create other chimeras consisting of protein kinase intracellular sequences, cDNA or genomic sequences encoding an extracellular domain of the receptor can be endowed with a restriction site introduced at a location just preceding the extracellular domain of choice. The extracellular domain fragment terminating in the restriction site can then be joined to the protein kinase sequences. Typical extracellular domains may be derived from receptors which recognize complement, carbohydrates, viral proteins, bacteria, protozoan or metazoan parasites, or proteins induced by them. Similarly, ligands or receptors expressed by pathogens or tumor cells can be attached to protein kinase sequences to direct immune responses against cells bearing receptors recognizing those ligands.

To identify the minimal protein kinase sequences necessary for cytolysis, a series of deletion mutants may be prepared by standard techniques in which successively more of the kinase intracellular domain is removed. Such deletion mutants are tested for efficacy in any of the assays described herein. Useful intracellular domains for the Syk protein kinase include, for example, amino acids 336–628 of the porcine Syk sequence and amino acids 338–630 of the human Syk sequence.

While the invention has been described in connection with specific embodiments thereof, it will be understood that it is capable of further modifications and this application is intended to cover variations, uses, or adaptations of the invention and including such departures from the present disclosure as come within the art to which the invention pertains and as may be applied to the essential features hereinbefore set forth as follows in the scope of the appended claims.

What is claimed is:

1. A proteinaceous chimeric receptor, comprising (a) an intracellular portion of a Syk protein-tyrosine kinase, (b) a transmembrane portion, and (c) an extracellular portion which is capable of specifically recognizing and binding a target cell or a target infective agent.

2. The receptor of claim 1, wherein said protein-tyrosine kinase is a human Syk kinase.

3. The receptor of claim 1, wherein said intracellular portion includes amino acids 336–628 of human Syk (SEQ ID NO: 5) or amino acids 338–630 of porcine Syk (SEQ ID NO: 6).

4. The receptor of claim 1, wherein said target infective agent is an immunodeficiency virus or said target cell is infected with an immunodeficiency virus.

5. The receptor of claim 1, wherein said extracellular portion comprises an HIV envelope-binding portion of CD4.

6. The receptor of claim 1, wherein said extracellular portion comprises the ligand-binding portion of a receptor, the receptor-binding portion of a ligand, the antigen-binding portion of an antibody, or a functional derivative thereof.

* * * * *

UNITED STATES PATENT AND TRADEMARK OFFICE
CERTIFICATE OF CORRECTION

PATENT NO. : 6,392,013 B1
DATED : May 21, 2002
INVENTOR(S) : Brian Seed, Charles Romeo and Waldemar Kolanus It is certified that error appears in the above-identified patent and that said Letters Patent is hereby corrected as shown below:

Title page,
Item [56], References Cited, OTHER PUBLICATIONS, "Reidel et al.," first reference, replace "2934" with -- 2943 --.

Column 2,
Line 51, replace "or" with -- of --;

Column 3,
Line 15, replace "gp120glycoprotein" with -- gp120glycoprotein --;

Column 8,
Line 27, replace "therapeutic:" with -- therapeutic --;

Column 17,
Line 18, replace "PIG" with -- FIG --;

Column 18,
Line 65, replace "Chan et:" with -- Chan et --;

Column 19,
Line 18, replace "performed,." with -- performed, --;

Column 21,
Line 51, replace "results;" with -- results --;

Column 23,
Line 3, replace "9107-91111" with -- 9107-9111 --;
Line 66, replace "9107-91111" with -- 9107-9111 --;

Column 24,
Line 61, unbold "30";

UNITED STATES PATENT AND TRADEMARK OFFICE
CERTIFICATE OF CORRECTION

PATENT NO.  : 6,392,013 B1
DATED       : May 21, 2002
INVENTOR(S) : Brian Seed, Charles Romeo and Waldemar Kolanus It is certified that error appears in the above-identified patent and that said Letters Patent is hereby corrected as shown below:

Column 28,
Line 36, replace "mRNA,." with -- mRNA. --;
Line 65, replace "Chan et:" with -- Chan et --;

Column 32,
Line 11, replace "336-628 of human Syk" with -- 338-630 of human Syk --; and
Line 12, replace "338-630 of porcine Syk" with -- 336-628 of porcine Syk --.

Signed and Sealed this

Tenth Day of February, 2004

JON W. DUDAS
*Acting Director of the United States Patent and Trademark Office*